United States Patent
Bandaru et al.

(10) Patent No.: US 6,635,425 B2
(45) Date of Patent: Oct. 21, 2003

(54) 5'-THIO PHOSPHATE DIRECTED LIGATION OF OLIGONUCLEOTIDES AND USE IN DETECTION OF SINGLE NUCLEOTIDE POLYMORPHISMS

(75) Inventors: Rajanikanth Bandaru, Corelville, IA (US); Gyanendra Kumar, Guilford, CT (US)

(73) Assignee: Molecular Staging, Inc., New Haven, CT (US)

( * ) Notice: Subject to any disclaimer, the term of this patent is extended or adjusted under 35 U.S.C. 154(b) by 0 days.

(21) Appl. No.: 09/910,372

(22) Filed: Jul. 20, 2001

(65) Prior Publication Data

US 2003/0044794 A1 Mar. 6, 2003

Related U.S. Application Data

(60) Provisional application No. 60/259,918, filed on Jan. 5, 2001.

(51) Int. Cl.[7] .......................... C12Q 1/68; C12P 19/34; C07H 21/02

(52) U.S. Cl. .......................... 435/6; 435/91.1; 536/23.1

(58) Field of Search .................... 435/6, 91.1; 536/23.1

(56) References Cited

U.S. PATENT DOCUMENTS

| | | | |
|---|---|---|---|
| 5,854,033 A | 12/1998 | Lizardi | 435/91.21 |
| 6,124,120 A | 9/2000 | Lizardi | 435/91.2 |
| 6,143,495 A | 11/2000 | Lizardi et al. | 435/6 |

FOREIGN PATENT DOCUMENTS

| | | |
|---|---|---|
| EP | 0756009 A2 | 1/1997 |
| WO | WO 97/19193 | 5/1997 |

OTHER PUBLICATIONS

Vroom et al., "Synthesis of cyclic oligonucleotides by a Modified Phosphotriester Approach," Nucleic Acids Research IRL Press Limited, vol. 16, No. 10, pp. 4607–4621 (1988).

Barbato et al., "Solid Phase Synthesis of Cyclic Oligodeoxyribonucleotides, Tetrahedron Letters" Pergamon Journals Ltd., vol. 28, No. 46, pp. 5727–5728 (Sep. 1987).

Prakash et al. "Molecular Recognition by Circular Oligonucleotides. Stron Binding of Single–stranded DNA and RNA,": J. Chem. Soc., pp. 1161–1163 (1991).

James et al. "Surprising Fidelity of template–directed chemical ligation of oligonucleotides," Chemistry & Biology, vol. 4, No. 8, pp. 595–605, 1997.

(List continued on next page.)

*Primary Examiner*—Jezia Riley

(57) ABSTRACT

The present invention provides a novel method for ligation of oligonucleotides containing 5'-phosphorothioates on complementary templates by the action of DNA ligases. This reaction is readily applied to the synthesis of a single stranded circular DNA containing a phosphorothioate linkage at the site of ligation junction. The efficiency of 5'-phosphorothioate directed ligation reaction by ATP dependent DNA ligase reaction is similar to conventional 5'-phosphate ligation. The utility of enzymatic ligation in probing specific sequences of DNA is also described. The present invention also provides a novel non-enzymatic ligation of 5'-phosphorothioates that has been applied to the synthesis of single strand phosphorothioate and phosphate circular DNA. A process for detecting the presence of a mismatch in an otherwise complementary pair of oligonucleotides is disclosed using an enzyme-based technique which shows the presence of a mismatch by failing to form a ligated single stranded DNA circle that can optionally be amplified using standard methods of rolling circle amplification.

22 Claims, 21 Drawing Sheets

Phosphorothioates as Isosteres of Phosphate

Phosphate

Rp

Phosphorothioate

Sp

OTHER PUBLICATIONS

Daubendiek et al., "Rolling–Circle RNA Synthsis: Circular Oligonucleotdies as Efficient Substrates for T7 RNA Polymerase," J. Amer. Chem. Soc., vol. 117, No. 29, pp. 7818–7819 (1995).

Gryaznov et al., "Template Controlled Coupling and Recombination of Oligonucleotide Blocks Containing Thiophosphoryl Groups," Nucleic Acids Res., vol. 21, No. 6, pp. 1403–1408 (Dec. 1992—revised Feb. 1993).

Eric et al., "Melting Behavior of a Covalently Closed, Single–Stranded, Circular DNA," Amer. Chem. Soc., vol. 28, No. 1, pp. 268–273 (1989).

Reese et al, "The H–phosphonate approach to the solution phase synthesis of linear and cyclic oligoribonucleotides," vol. 27, No. 4, pp. 963–971 (1999).

Diegelman et al. "Generation of Circular RNAs and trans–cleaving catalytic RNAs by Rolling Trans. of Circular DNA oligo. Encoding Hairpin Ribozymes," vol. 26, No. 13, pp. 3235–3241 (1998).

Rubin et al., "Convergent DNA synthesis: a non–enzymatic Dimerization Approach to Circular oligodeoxynucleotides," Nucleic Acid Research vol. 23, No. 17, pp. 3547–3553 (1995).

Xu et al., "Nonenzymatic autoligation in Direct Three–color Detection of RNA and DNA Point Mutations," Nature Biotechnology vol. 19 (Feb. 2001). pp. 148–152.

Fire et al., "Rolling Replication of Short DNA Circles," Proc. Nat'l. Acad. Sci., vol. 92, pp. 4641–4645 (May 1995).

Nilsson er al., "Padlock Probes: Circularizing Oligonucelotides for Localized DNA Detection," Science, vol. 265, (Sep. 30, 1994).

Doherty et al., "Structural and Mechanistic Conservation in DNA Ligases," Nucleic Acids Research Oxford University Press, vol. 28, No. 21, pp. 4051–4058 (2000).

Bryant, et al., "Phosphorothioate Substrates for T4 RNA Ligase," Biochemistry, pp. 5877–5885 (1982).

Schweitzer et al., "Immunoassays with Rolling Circle DNA Amplification: A Versatile Platform for Ultrasensitive Antigen Detection," PNAS vol. 97, No. 18, pp. 10113–10119 (Aug. 29, 2000).

Dolinnaya et al., "Oligonucleotide Circularization by Template–Directed Chemical Ligation," Nucleic Acids Research Oxford University Press, vol. 21, No. 23, pp. 5403–5407 (1993).

Kanaya et al., "Template–Directed Polymerization of Oligoadenylates Using Cyanogen Bromide," Biochemistry pp. 7423–7430 (1986).

Wemmer et al., "Preparation and Melting of Single Strand Circular DNA Loops," Nucleic Acids Research IRL Press Limited, vol. 13, No. 23 (1985).

Capobiancol et al., "One Pot Solution Synthesis of Cyclic Oligodeoxyribonucleotides," Nucleic Acids Research Oxford University Press, vol. 18, No. 19, (1990).

Schenk et al., "The Accessibility of Thiophosphorylated Groups in DNA Fragmenzymatic Activity of Ligases and Restriction Endonuclease Bbs," Biochem Mol Biol. Int's., (Aug. 1995)—Abstract.

Lizardi et a., "Mutation Detection and Single–Molecule Counting Using Isothermal Rolling–Circle Amplification", Nature Genetics, vol. 19, pp. 225–232, Jul. 19, 1998.

Christian et al., "Detection of DNA Point Mutations and mRNA Expression Levels by Rolling Circle Amplifications in Individual Cells", PNAS, vol. 98, No. 25, pp. 14238–14243, Dec. 4, 2001.

Phosphorothioates as Isosteres of Phosphate

Phosphate

Phosphorothioate

Rp

Sp

ATP-dependent DNA Ligase Mechanism:

E + pppA ⇌ EpA + PPi

EpA + pDNA ⇌ AppDNA + E

DNA$_{OH}$ + AppDNA ⇌ DNApDNA + pA

NAD$^+$-dependent DNA Ligase Mechanism:

E + NAD$^+$ ⇌ EpA + NMN$^+$

EpA + pDNA ⇌ AppDNA + E

DNA$_{OH}$ + AppDNA ⇌ DNApDNA + pA

Common Phosphoramidate Intermediate

A

B

Lanes from left to right are:

1- 10 bp marker
2- linear MSI 789-5'PO linear circle 4.2
3- linear MSI 894 - 5' PS linear circle 4.2
4- MSI 789 + PA 83 (correct guide)-30 min
5- MSI 789 + PA 83 (correct guide)-1 hr
6- MSI 894 + PA 83 (correct guide )- 30 min
7- MSI 894 + PA 83 (correct guide) - 1 hr
8- MSI 789 + Mu-G-C4.2 guide-30 min
9- MSI 789 + Mu-G-C4.2 guide-1 hr
10- MSI 894 + Mu-G-C4.2 guide -30 min
11- MSI 894 + Mu-G-C4.2 guide 1 hr 1- 10bp marker
2- linear MSI 789-5'PO linear circle 4.2
3- linear MSI 894 - 5' PS linear circle 4.2
4- MSI 789 + Mu-C4.2 guide-30 min
5- MSI 789 + Mu-C4.2 guide -1hr
6- MSI 894 + Mu-C4.2 guide-30 min
7- MSI 894 + Mu-C4.2 guide-1hr
8- MSI 789 + Mu-T-C4.2 guide -30 min
9- MSI 789 + Mu-T-C4.2 guide-1hr
10- MSI 894 + Mu-T-C4.2 guide-30 min
11- MSI 894 + Mu-T-C4.2 guide -1 hr
12- MSI 789 + No Guide - 30 min
13- MSI 789 + No Guide - 1 hr
14 - MSI 894 + No Guide - 30 min
15- MSI 894 + No Guide - 1 hr 1. 10 bp marker
2. linear circle 4.2-5'PO-msi 789, 2 hours
3. linear circel 4.2- 5'PS - msi 894, 2 hours
4. msi 789 + PA 83 (correct guide), 2 hours
5. msi 894 + PA 83 (corrcet guide), 2 hours
6. msi 789 + MuT. C 4.2 guide, 2 hours
7. msi 894 + MuT. C. 4.2 guide, 2 hours
8. msi 789 + Muc-c.4.2 guide, 2 hours
9. msi 894 + Muc.c4.2 guide, 2 hours
10. msi 789 + MuG.C 4.2 guide, 2 hours
11. msi 894 + MuG. C 4.2 guide, 2 hours
12. msi 789 + no guide, 2 hours
13. msi 894 + no guide, 2 hours … # 5'-THIO PHOSPHATE DIRECTED LIGATION OF OLIGONUCLEOTIDES AND USE IN DETECTION OF SINGLE NUCLEOTIDE POLYMORPHISMS This application claims priority of U.S. Provisional Application Serial No. 60/259,918, filed Jan. 5, 2001, the disclosure of which is hereby incorporated by reference in its entirety.

FIELD OF THE INVENTION

The present invention relates generally to the field of ligation of nucleic acids, using phosphorothioate derivatives as a means of ligating single stranded oligonucleotides, and where such oligonucleotides contain a point mutation, as a means of detecting single nucleotide polymorphisms.

BACKGROUND OF THE INVENTION

The ability to detect single base differences in DNA is of great importance in molecular genetics. Specific identification of point mutations is playing an increasingly important role in diagnosis of hereditary disease and in identification of mutations associated with drug resistance. Because of the high fidelity of ligation, enzymatic ligation methods have proven useful in a number of novel gene detection techniques.

Polynucleotide ligases are ubiquitous cell proteins that are required for a number of important cellular processes, including replication, repair and recombination of DNA. One of the best-characterized enzymes that joins DNA ends is T4 DNA ligase, first isolated some three-decades ago (for reviews see 1–3). This and related proteins catalyze ATP-dependent phosphodiester bond formation between the 5'-phosphate and 3'-hydroxyl groups of adjacent DNA strands (4,5). Duplex DNA molecules with either cohesive ends or blunt ends can serve as ligation substrates (6,7). T4 DNA ligase can also repair nicked DNA duplexes efficiently and thus the enzyme is often used for joining two DNA segments that are hybridized adjacent to each other on a complementary strand.

The use of circular DNAs (which can be formed by ligation, internal or external, of single stranded oligonucleotides) in such methods of amplification as rolling circle amplification technology (RCAT™) promises to greatly improve the performance of gene-based diagnostic testing and to facilitate the detection of a wide variety of infectious agents, cancerous cells, and genetic variations (also called polymorphisms) (71). Since the discovery of circular DNA to serve as a template for DNA polymerases (72), there has been increasing demand for the synthesis of circular oligonucleotides. Although there have been reports of successful enzymatic ligation to produce circular DNA, the yields of circles (less than 100 nucleotides or 100 nt) have been modest. Non-enzymatic ligation strategies have been somewhat more successful in the synthesis of small circular DNAs (less then 50 nt) on solid supports. Several approaches using non-enzymatic methods have recently been described. However, synthesis of circular DNA (larger than 50 to 100 nt or nucleotides) by non-enzymatic methods is a slow, entropically disfavored process and remains a synthetic challenge.

Kool et al have reported a method of circle synthesis (See Kool, E. T. et. al, Nature Biotechnol (2001)19, pp. 148–152; Kool, E. T. et. al., *Nucleic Acids Res,* (1995)I. 23 (17), pp. 3547–355; Kool, E. T. et.al (1999) 27(0.3), pp 875–871. However, Kool's published report uses a chemical ligation approach wherein the ligation reaction produces a DNA containing sulfur in the bridging junction as 5'-S-thioester linkage at the site of ligation. In this approach, two oligonucleotides bound at adjacent sites on a complementary strand undergo autoligation by displacement of a 5'-iodide with 3'-phosphorothioate group (see, in general, the cited references herein). In addition, Kool et. al has reported a reagent free autoligation approach where 5'-S-thioester bonds formation between 3'-phosphorothioate and a 5'-iodide, which acts as a leaving group.

Other published methods report a chemical ligation approach for the synthesis of single stranded circular DNA wherein the modified circular DNA comprises a single 5'-S-thioester linkage with sulfur located in the 5'-bridging region. Other strategies have used sulfur atoms to replace specific non-bridging phosphate oxygens in RNA. Eckstein, F, *Angew. Chem. Intl. Ed. Engl.* 22, pages 423 (1993) have synthesized phosphorothioate-linked polyribonucleotides as early as 1967 using DNA-dependent RNA polymerase from *E.coli*. Several other polymerases proved useful in the synthesis of the phosphorothioate linked ribo and deoxy oligonucleotides.

When a single base pair mismatch exists at either side of the ligation junction, the efficiency of the enzyme in ligating the two oligonucleotides decreases markedly. This high sequence selectivity has resulted in the development of novel sequence detection methods using this enzyme. These approaches include the ligase detection reaction (LDR) (8–10) and the ligase amplification reaction (LAR) (11). T4 DNA ligase displays selectivity against single base mismatches on the order of 2 to 6 fold in yield and conditions such as the presence of spermidine, high salt and low enzyme concentration have been reported to improve the fidelity of ligation to as high as 40 to 60-fold (9, 10). The thermostable DNA ligase from *Thermus thermophilus* (Tth DNA ligase) has been reported to have higher fidelity (mismatch discrimination of 450 to 1500-fold in rate) and has been measured for the wild-type enzyme with optimized mismatch location at the 5'-side of junction (12,13), making its use preferable in some sequence detection methods including the ligase chain reaction (14–16).

Since the discovery of ligases there have also been developed a number of non-enzymatic approaches to joining the ends of two DNA strands (17–29). These chemical ligations have been achieved via oxidative coupling of terminal 3'-phosphorothioates and displacement of 5'-bromide from a monoacetylamino bromide (19), 5'-tosylate (17) and a 5'-iodide (30). The resulting DNA contains the modified 5'-S-thioester linkage in the bridging position. Strategically placed sulfur atoms in the backbone of nucleic acids have found widespread utility in probing of specific interactions of proteins, enzymes and metals. Sulfur replacement for oxygen has also been carried out at the 2'-position of RNA (37–39) and in the 3'-5'-positions of RNA (40–45) and of DNA (46–56) Polyribonucleotide containing phosphorothioate linkages were obtained as early as 1967 by Eckstein et al. using DNA-dependent RNA polymerase from *E.coli* (57). DNA-dependent RNA polymerase is a complex enzyme whose essential function is to transcribe the base sequence in a segment of DNA into a complementary base sequence of a messenger RNA molecule. Nucleoside triphosphates are the substrates that serve as the nucleotide units in RNA. In the polymerization of triphosphates, the enzyme requires a DNA segment that serves as a template for the base sequence in the newly synthesized RNA. In the original procedure, Uridine 5'-O-(1-thiotriphosphate), adenosine 5'-O-triphosphate, and only d (AT) as a template was used. As a result, an alternating copolymer [Ap (S) UpAp (S) Up] is obtained, in which every other phosphate was replaced by a phosphorothioate group. Using the same approach and uridine 5'-O-(1-thiotriphosphate) and adenosine 5'-O-(1-thiotriphosphate), polyribonucleotide containing an all phosphorothioate backbone was also synthesized (58). In both cases, nucleoside 5'-O-(1-thiotriphosphates) as a mixture of two diastereomers were used.

The stereo chemical course of polymerization catalyzed by *Escherichia coli* polymerase was determined by Eckstein et al using the 1-thio-analog of adenosine 5'-O-triphosphate as a substrate (58,59). The Sp isomer was found to serve as an enzyme substrate and was further used with Uridine 5'-O-triphosphate and a DNA template of poly-d (AT). The resulting RNA polymer was the complementary alternating copolymer of adenosine and uridine linked by alternating 3'-5'-phosphodiester and 3'-5'-phosphorothioate bonds. Other polymerases useful in the synthesis of the phosphorothioate backbone bearing polyribonucleotides and polyrdeoxyibonucleotides have been described (60–68).

In addition, Single Nucleotide Polymorphisms (SNPs) have been characterized using a variety of methods. Such methods include the direct or indirect sequencing of the site, the use of restriction enzymes where the respective alleles of the site create or destroy a restriction site, the use of allele specific hybridization probes, the use of antibodies that are specific for the proteins encoded by the different alleles of the polymorphism, or by other biochemical interpretation. However, no assay yet exists that is both highly accurate and easy to perform.

Oligonucleotide ligation assay (OLA) is an assay proposed for SNP determination [Landergen et al., *Science* (1988) 241:1077–1080]. The OLA protocol uses two oligonucleotides, which are designed to be capable of hybridizing to abutting sequences of a single strand of a target. One of the oligonucleotides is biotinylated, and the other is detectably labeled. If the precise complementary sequence is found in a target molecule, the oligonucleeotides will hybridize such that their termini abut, and create a ligation substrate. Ligation then permits the labeled oligonucleotide to be recovered using avidin, or another biotin ligand. OLA is capable of detecting point mutations [Nickerson, D. A. et. al., Proc. Natl. Acad. Sci. U.S.A., (1990) 87:8923–8927]. In this method, PCR is used to achieve the exponential amplification of target DNA, which is then detected using OLA. Assays, such as OLA, require each candidate dNTP of a polymorphism be separately examined, using a separate set of oligonucleotides for each dNTP. The major drawback is that ligation is not a highly discriminating process and non-specific signals can be a significant problem.

Since phosphorothioates exist as diastereomers, automated synthesis of DNA on solid phase synthesizers results in mixtures of Rp and Sp diastereomers at the individual phosphorothioate linkages. Replacement of oxygen with a sulfur atom in 5'-phosphate of DNA results in increased bond length, reduced electronegativity and increased bond length. In addition, sulfur substitution for oxygen should also result in reduced hydration and altered metal ion affinity. Hence, these physico-chemical changes could have significant effect on any of the three fundamental steps in enzymatic ligation.

The major advantages of the present invention over other methods, including the autoligation approach, include the following: the autoligation approach produces a single 5'-S-thioester linkage where the sulfur is located in the 5'-bridging region whereas the procedures of the present invention do not—the sulfur is outside of the bridge so that the 5'-thio phosphate directed ligation as disclosed herein produces a circular DNA with sulfur being located in the non-bridging region of phosphorothioate at 5'-end of the incipient circle; prior art approaches include the reagent free autoligation method whereas the present invention is enzyme based and provides great sensitivity to the presence of nucleotide mismatches; and the sulfur atom introduced in the processes of the invention resides in the non-bridging position which is isosteric to the naturally occurring phosphate linkage and therefore does not interfere with subsequent uses of the circular product (such as subsequent rolling circle amplification). In sum, the current method is diastereo-selective approach and has great potential for allele discrimination.

BRIEF SUMMARY OF THE INVENTION

In one aspect, the present invention relates to a method for the ligation of nucleic acids that is at once efficient, low cost and amenable for large-scale ligation of DNA and analogs thereof, for use as probes, diagnostic agents, and therapeutic agents.

It is one object of the present invention to provide closed circles formed by the processes of the invention wherein said circles contain a phosphorothioate linkage but are useful in many, if not all, of the same processes for which conventional single-stranded closed circles find use because the circles contain phosphodiester bonds wherein the sulfur atom is not part of the bridging atoms.

It is another object of the present invention to provide a process for rolling circle amplification (RCA) employing as templates the single stranded circles formed by the methods of the invention and thereby amplifying selected nucleotide sequences.

In another aspect, the present invention relates to a process for detecting nucleotide mismatches, such as in single nucleotide polymorphisms (SNPs), comprising:

contacting a first oligonucleotide, comprising first and second segments, with a second oligonucleotide wherein said second oligonucleotide comprises a first complementary segment, a second complementary segment, and a third segment and wherein said second oligonucleotide also comprises a phosphorothioate at its 5'-terminus, and wherein said first and second complementary segments of said second oligonucleotide are complementary to the first and second segments of said first oligonucleotide one of which first oligonucleotide segments comprises at least one mismatched nucleotide, and wherein said third segment is not complementary to said first oligonucleotide, and wherein said contacting occurs under conditions promoting hybridization of said first and second segments with said first and second complementary segments, and wherein said hybridization results in the formation of a complex in which the 5'- and 3'-ends of said second oligonucleotide are adjacent to each other, and said 3'-nucleotide may be opposite a mismatched nucleotide of said first oligonucleotide, contacting said hybridized complex with a ligation catalyst under conditions promoting ligation of the 5'- and 3'-ends of said second oligonucleotide in said hybridized complex when said mismatch is not present, and detecting formation of ligated second oligonucleotide wherein reduced or non-formation thereof indicates the presence of a nucleotide mismatch.

In a preferred embodiment of this process, the catalyst is an enzyme, most preferably Ampligase or T4 DNA or RNA ligase. For RNA ligations, see Faruqi, U.S. application Ser. No. 09/547,757, filed Apr. 12, 2000, the disclosure of which is hereby incorporated by reference in its entirety.

In another aspect, the present invention relates to a detection process for single nucleotide polymorphisms as described herein but further comprising detecting the occurrence of ligated second oligonucleotide by contacting the third segment of ligated second oligonucleotide with a primer oligonucleotide complementary to said third segment under conditions promoting hybridization of said primer to said third segment and further contacting said complex with a rolling circle amplification (RCA) enzyme under conditions promoting rolling circle amplification of said ligated second oligonucleotide. Here, the first oligonucleotide could be derived from genomic DNA.

24); (5). Chemically ligated phosphorothioate reference circle (SEQ ID NO: 25); (6). No Circle control; (7). No bridge control (SEQ ID NO: 22) RCA reaction [although lane 7 shows the presence of RCA product in control experiment, this is likely due to the presence of traces of bridge (BO), which is also a primer as a contaminant in the purified circle for RCA. However, if the RCA reaction is carried out for 2 hours instead of 20 hours, no such product is observed in lane 7.

Figure 15:
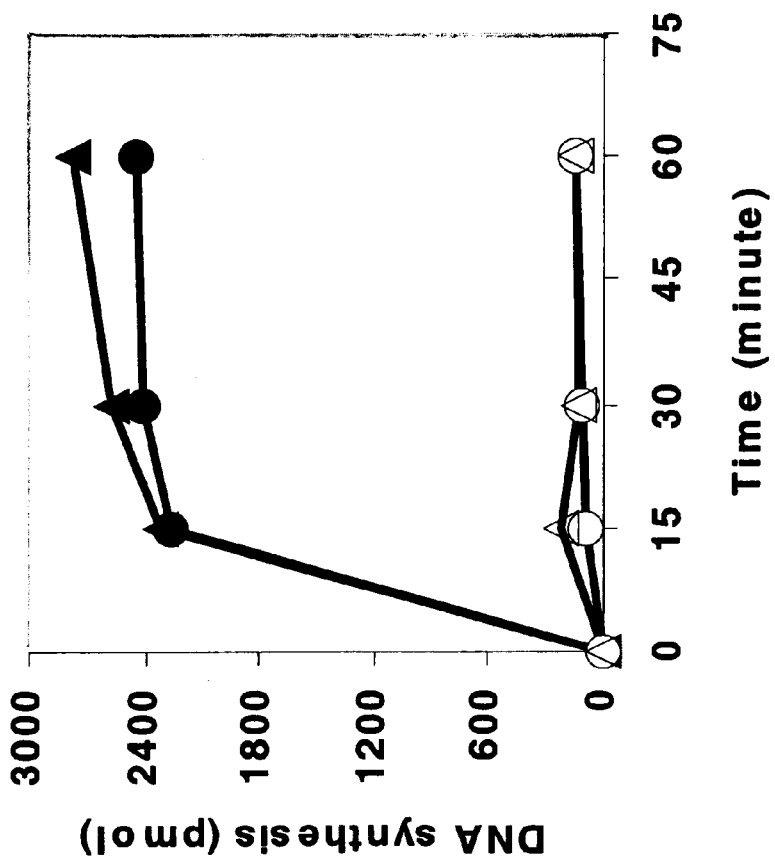

FIG. 15 shows the results of rolling circle amplification (RCA) reactions containing 25 fmol of the pre-annealed DNA circles (SEQ ID NO: 24 or 25) and primer (SEQ ID NO: 28 or 29) (2 pmol as nucleotides), 1 mM each of dTTP and dGTP, and 1 mM [$\alpha$-$^{32}$P] dCTP (150–300 cpm/pmol), 2.2 µg of E.coli SSB (Promega) and 10 Units/µl of T7 DNA polymerase in 25 µl reaction buffer containing 20 mM Tris-HCl (pH 7.5), 10 mM MgCl$_2$, 25 mM NaCl. Additions were performed on ice and then shifted to 37° C. Replication products were quantitated by spotting onto DE81 filters as described by Fan, Linhua, Davey, M J, and O'Donnell, M, 1999, *Molecular Cell*, Vol. 4, 541–553.

Figure 16:
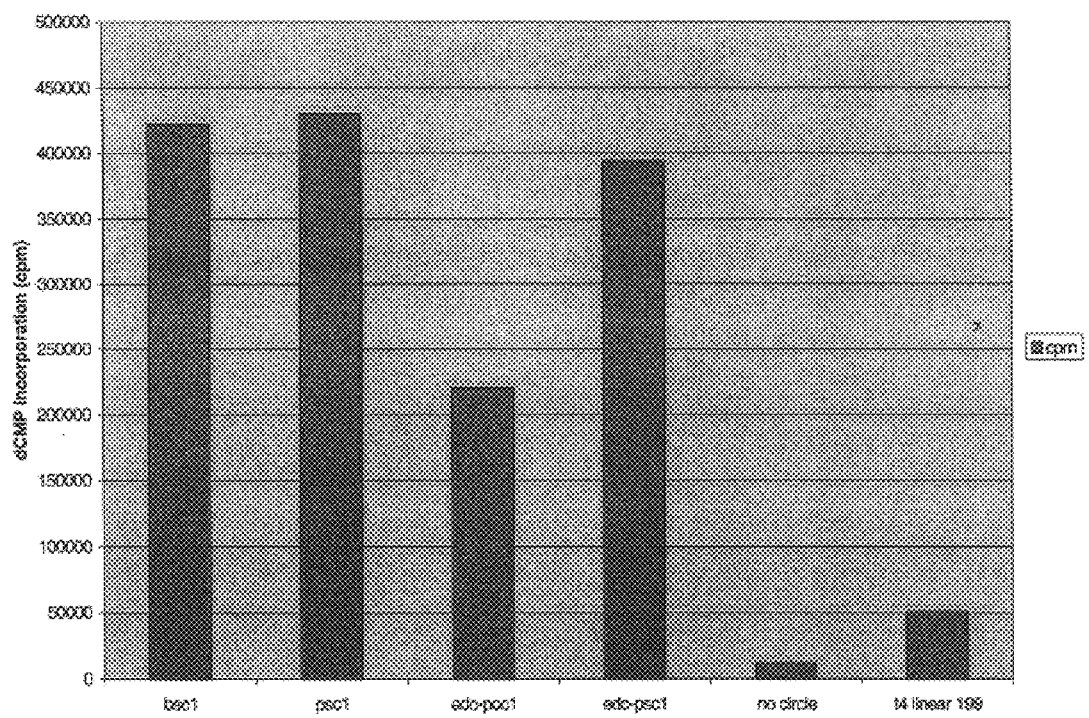

FIG. 16 shows measurement of efficiency of RCA reaction by [$\alpha$-P$^{32}$] dCTP incorporation. Reactions were carried out in 20 µl of total volume containing 50 nm of circular DNA templates (SEQ ID NO: 24 or 25), 1 µM of rolling-circle primer (SEQ ID NO: 28 or 29), in 50 mM Tris-HCl (pH 7.5), 10 mM MgCl$_2$, 20 mM ammonium sulfate, 1 mM each of dATP, dGTP, dTTP and 1 µCi/20 µl of [P$^{32}$] dCTP, 5% glycerol, 4 ng/ml of yeast pyrophosphotase and phase $\phi$-29 DNA polymerase was added last at a concentration of 10 U/µl (approximately 100 nM). The reactions were incubated at 37° C. for 20 hours. After 20 hours the reaction was stopped by the addition of 10 mM EDTA. A. Enzymatic phosphate circle (SEQ ID NO: 24). B. Enzymatic Phosphorothioate Circle (SEQ ID NO: 25). C. Chemically ligated phosphate circle (SEQ ID NO: 24). D. Chemically ligated phosphorothioate circle (SEQ ID NO: 25). E. No circle 1 control reaction. F. No open circle oligo (SEQ ID NO: 18) reaction.

Figure 17:
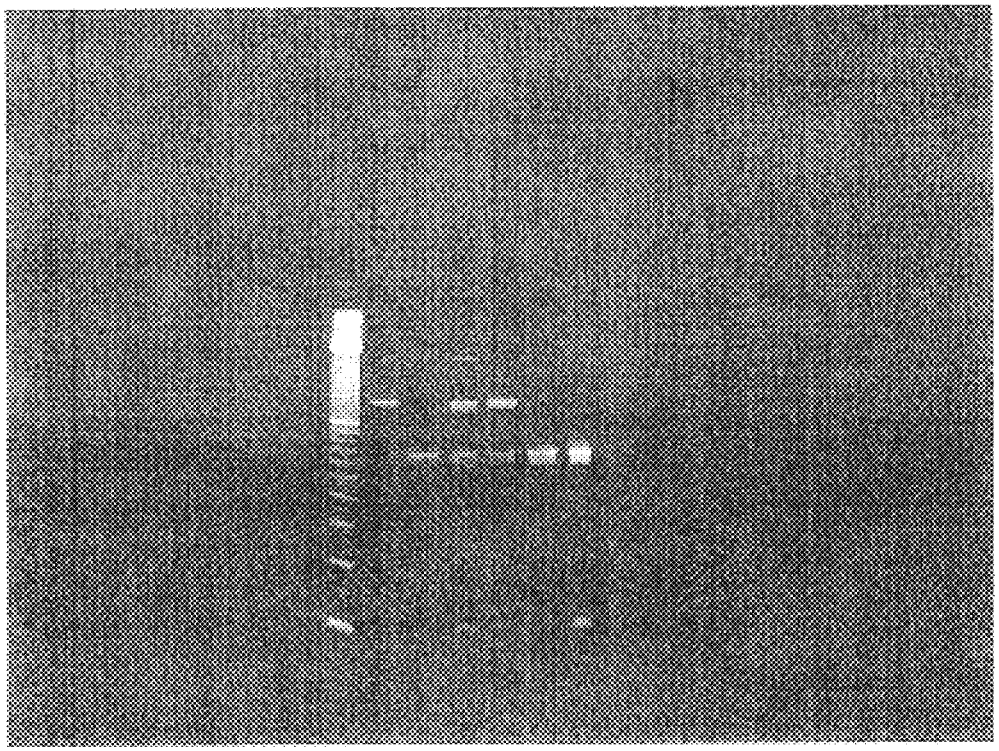

FIG. 17 shows an analysis of chemical ligation reaction products by 15% TBE-Urea PAGE: Lanes from left to right are: (1). 10 bp marker from Gibo-BRL; (2). Enzymatic reference circle (7); (3). 5'-Phosphorothioate 80mer open circle oligo (SEQ ID NO: 19); (4). 5'-Phosphate 80mer opene circle oligo (SEQ ID NO: 18) ligation with EDC; (5). 5'-Phosphorothioate 80-mer open circle oligo (SEQ ID NO: 19) ligation with EDC; (6). No bridge (SEQ ID NO: 22) control reaction with SEQ ID NO: 19; (7). No EDC control ligation reaction with SEQ ID NO: 19.

Figure 18:
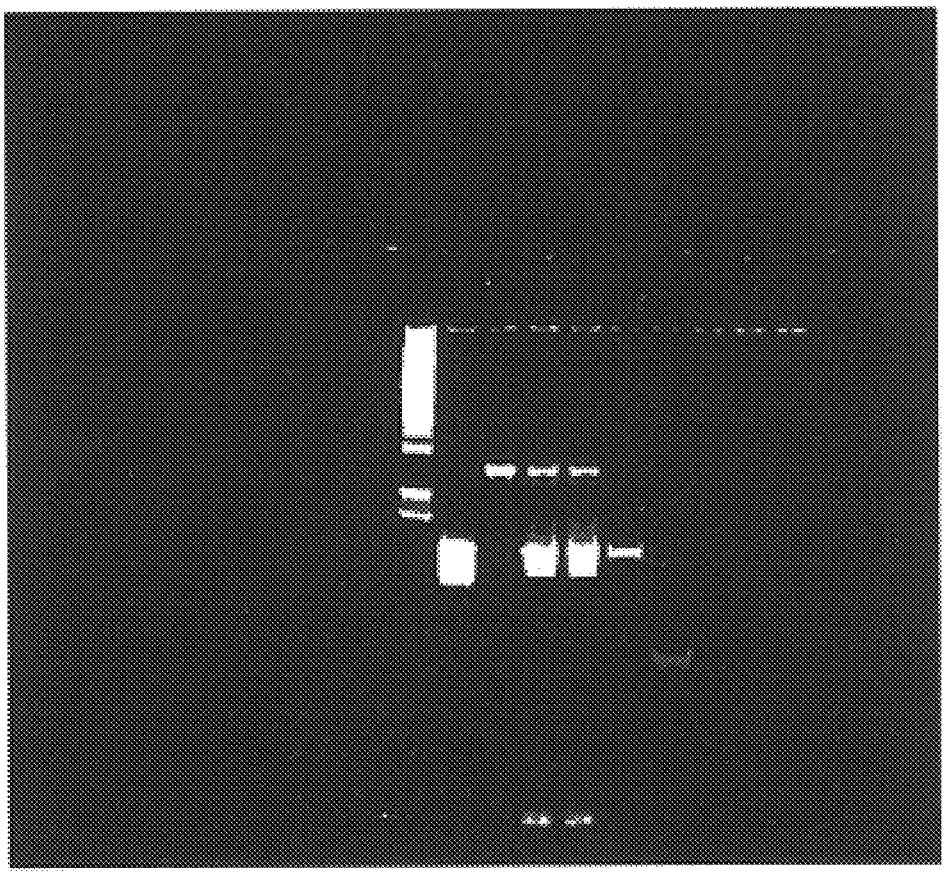

FIG. 18 shows results of an analysis of chemical ligation carried out in presence of ATP by 15% TBE-Urea PAGE: Lanes from left to right are: (1), 10 bp marker, (2) open circle oligo (SEQ ID NO: 18); (3) reference circle (SEQ ID NO: 24), (4) 5'-Phosphate open circle oligo (SEQ ID NO: 18) in presence of ATP, (5) 5'-Phosphorothioate open circle oligo (SEQ ID NO: 19) chemical ligation reaction in the presence of ATP, (6) 5'-Phosphate open circle oligo (SEQ ID NO: 18) chemical ligation reaction in the absence of ATP.

Figure 19:
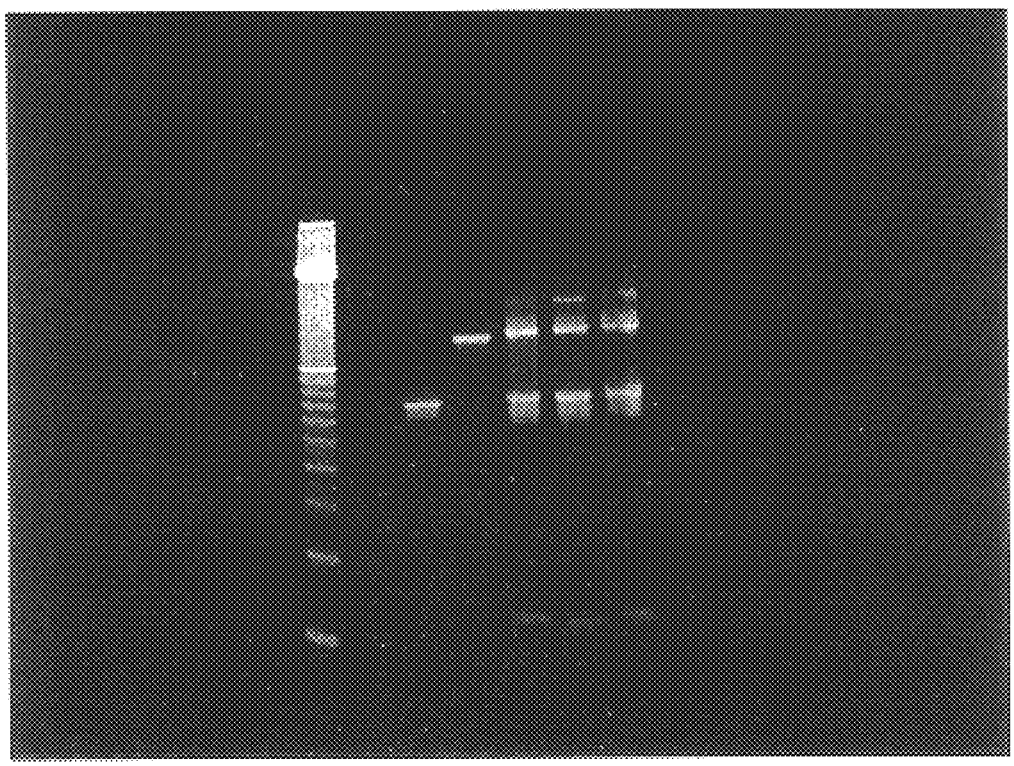

FIG. 19 shows the effect of metal ion on chemical ligation of open circle oligo (OCO) in presence of a bridge oligo (BO) using EDC: The gel was stained with Gel Star (FMC) for 30 minutes at room temperature. Lanes left to right are: Lane 1, 10 bp marker, Lane 2 linear OCO (SEQ ID NO: 18); Lane 3 reference circle (SEQ ID NO: 24); Lane 4. 5'-Phosphorothioate open circle oligo (SEQ ID NO: 19) chemical ligation reaction product in presence of MgCl$_2$, Lane 5. 5'-Phosphorothioate open circle oligo (SEQ ID NO: 19) chemical ligation reaction product in the presence of MnCl$_2$, Lane 6. Phosphorothioate open circle oligo (SEQ ID NO: 19) chemical ligation reaction product in the presence of NiCl$_2$.

Figure 20:
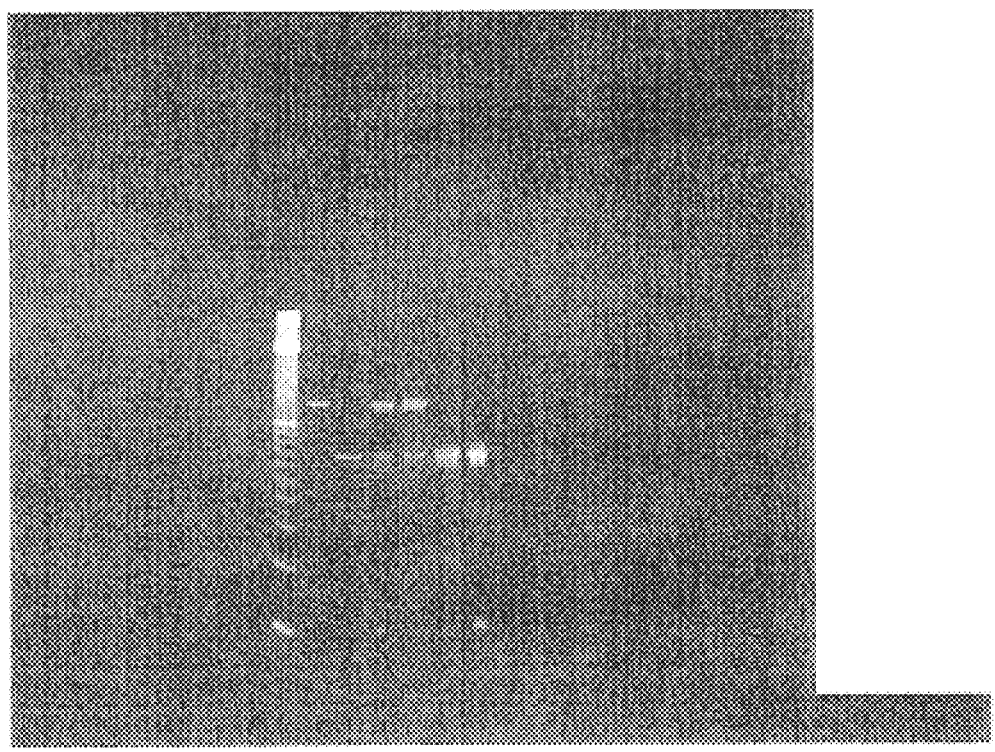

FIG. 20 shows the metal ion on T4 DNA Ligase catalyzed enzymatic ligation of open circle oligo (SEQ ID NO: 18) in presence of a bridge oligo (SEQ ID NO: 22): Lanes from left to right are: (1). 10 bp marker from Gibo-BRL; (2). Reference circle oligo (SEQ ID NO: 24); (3). 5'-Phosphorothioate open circle oligo (SEQ ID NO: 19) (4). 5'-Phosphorothioate open circle oligo (SEQ ID NO: 19) enzymatic ligation reaction product in presence of MgCl$_2$; (5) 5'-Phosphorothioate open circle oligo (SEQ ID NO: 19) enzymatic ligation reaction product in presence of MnCl$_2$, (6) 5'-Phosphorothioate open circle oligo (SEQ ID NO: 19) enzymatic ligation reaction product in presence of NiCl$_2$ (7). No metal ion negative control with 5'-phsophorothioate open circle oligo (SEQ ID NO: 19).

Figure 21:
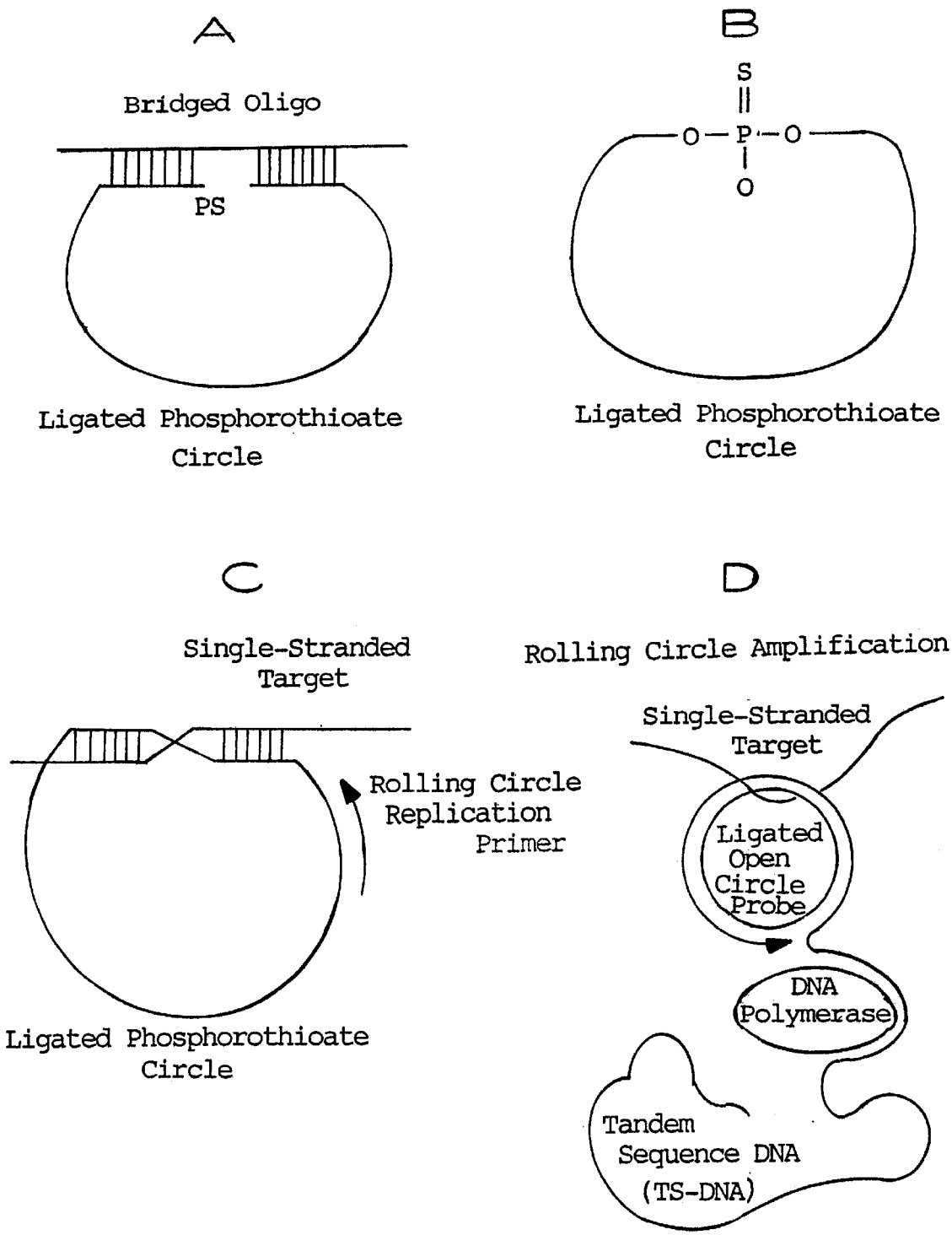

FIG. 21 shows circularization by ligation, and amplification by rolling circle amplification. A. Pre-circularization oligo with 5'-phosphorothioate annealed to a bridge oligo with concomitant ligation by DNA ligase. B. Ligated circle containing a single phosphorothioate. C. Ligated phosphorothioate circle and binding of complementary primer for rolling circle amplification. The primer 3'-end is located five or six bases away from the last paired base in the hybridized probe arm. D. Rolling circle amplification of the circular probe, catalyzed by a strand displacing DNA polymerase.

DETAILED DESCRIPTION OF THE INVENTION

Figure 3:
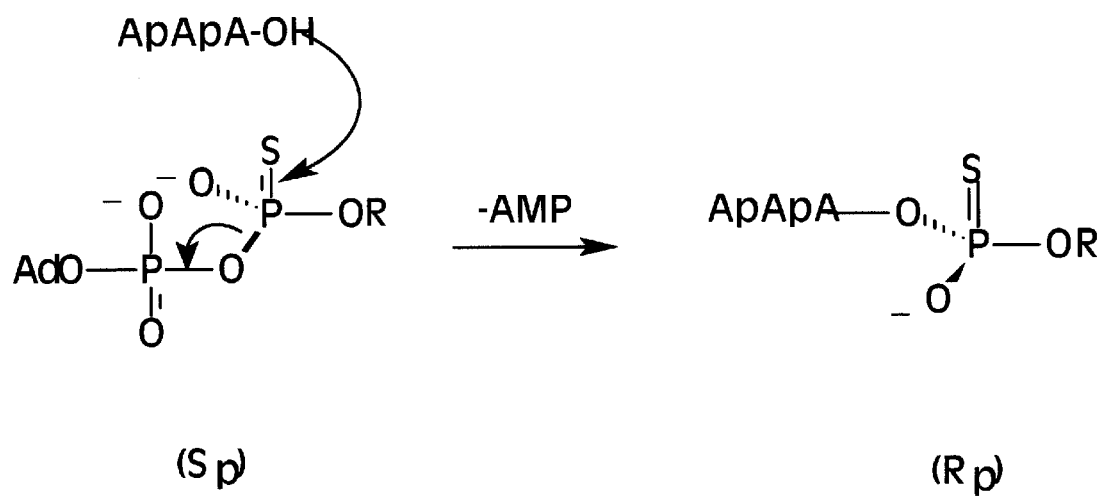
FIG. 3 shows several reactions in the formation of phosphorothioates. Panel A shows formation and Panel B shows a completed bond or bridging structure with the sulfur atom outside of the bridge.
Figure 3:
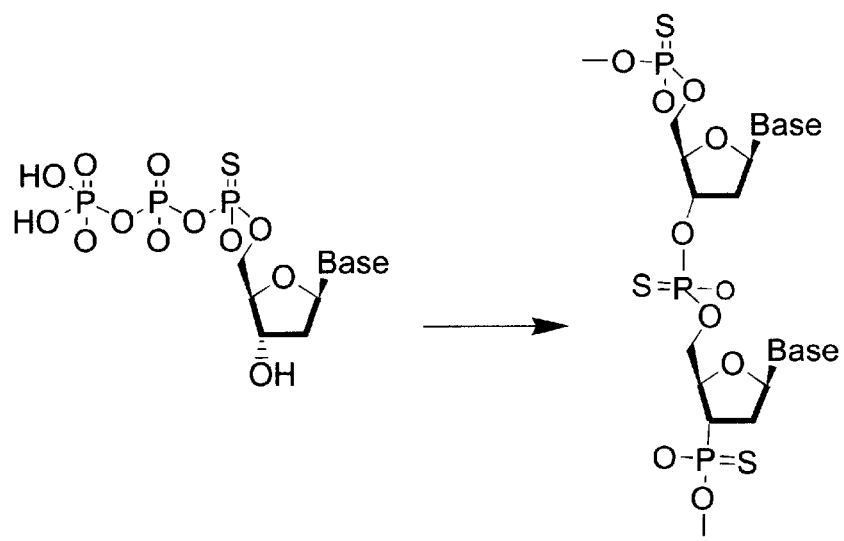
Figure 4:
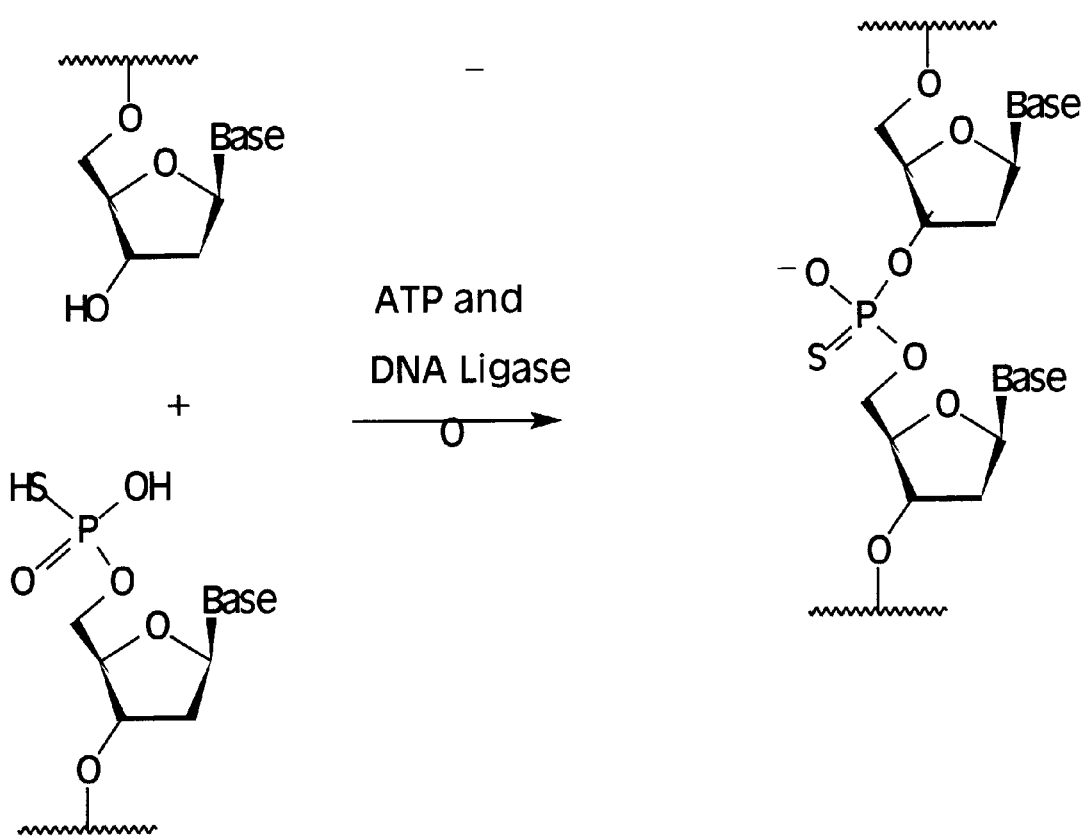
FIG. 4 shows the enzymatic ligation of 5'-phosphorothioates. The enzymatic ligation of 5'-phosphorothioates was achieved by annealing with complementary short bridge oligo in DNA ligase under standard ligation conditions. The non-enzymatic/chemical ligation was achieved in the presence of a coupling agent (such as EDC).

The present invention relates to methods for the ligation of nucleic acids that is at once efficient, low cost and amenable for large-scale ligation of DNA and analogs thereof, for use as probes, diagnostic agents, and therapeutic agents. The process of the invention forms a 3'-5' phosphorothioate linkage between the 3'-hydroxyl and 5'-phosphorothioate group of a single strand DNA (FIGS. 3 and 4). In one embodiment, the process of forming such linkage may be ATP dependent.

In accordance with the foregoing, the present invention relates to a process for forming a single stranded circular oligonucleotide comprising contacting the 3'-hydroxyl and 5'-phosphorothioate groups of an open circle oligonucleotide (OCO), i.e., an open circle probe (OCP), wherein said OCO or OCP has such groups, in the presence of a bridging oligonucleotide (BO), said bridging oligonucleotide comprising nucleotide sequences complementary (in keeping with the conventional Watson-Crick hydrogen bonded base pairing scheme) to nucleotide sequences at or near the 3'- and 5'-ends of the OCO such that the bridging oligonucleotide can hybridize to said OCO complementary sequences and hold the ends of said OCO in position for ligation, thereby facilitating the formation of a closed circular oligonucleotide containing a 3'-5'-phosphorothioate linkage. In a preferred embodiment, said BO complementary nucleotide sequences are complementary to terminal stretches of nucleotides making up the OCO and thus include nucleotides complementary to either the 3'-nucleotide or the 5'-nucleotide or both nucleotides of said OCO (as shown in FIG. 21).

The OCO can thus act as a probe (i.e., an open circle probe (OCP)) for a target oligonucleotide, such as the bridging oligonucleotide (BO) disclosed herein and where this target oligonucleotide can include genomic DNA so that the OCO (or OCP) thereby acts as a probe for genomic DNA (such as where the genomic DNA contains a single nucleotide polymorphism).

The processes according to the present invention rely on formation of an ATP-dependent 3'-5' phosphorothioate linkage between the 3'-hydroxyl and 5'-phosphorothioate group of a single strand DNA using an enzyme, such as T4 DNA ligase (FIG. 4). Importantly, the resulting bonds are actual phosphodiester bonds wherein the sulfur atom is not part of the bridging atoms. As used herein, the term "bridging atoms" refers to those atoms forming part of the phosphodiester backbone of the resulting phosphodiester bond (thus, these include -----3'C—O—P—O-5'C----- and with the sulfur atom attached only as a side group to the phosphorus is not part of the bridging atoms.

In specific embodiments, the process of the invention is carried out in the presence of an enzyme, preferably a ligase, most preferably T4 DNA ligase. Where T4 ligase is used, adenosine 5'-triphosphate (ATP) is also present in the reaction medium.

Following formation of the closed circular oligonucleotide (CCO), the bridging oligonucleotide (BO) may be removed, such as by melting or by exonuclease treatment known in the art. Where the closed circular products of the invention are to be used a substrate for rolling circle amplification (RCA), said amplification will itself normally remove the bridging oligonucleotide during the first round of amplification. Alternatively, the process of the present invention may further comprise a step of removing the bridging oligonucleotide from the closed circular oligonucleotide, such as by first dissociating the BO from the closed circular oligonucleotide ligation product.

In one embodiment, the process of the invention may employ a step wherein said OCO and said BO are annealed prior to contacting said 3'-OH and 5'-phosphorothioate groups. Alternatively, they may be allowed to anneal as part of the reaction procedure.

In separate embodiments of the present invention, said BO and said OCO are present in the mole ratio of about 1 to 1.2, respectively. Alternatively, the molar concentration of BO is greater than that of OCO. In a highly specific example, the ratio of BO to OCO may be about 1.2.

The process of the claimed invention includes embodiments wherein said OCO and said BO are deoxyribonucleotides or ribonucleotides.

The present invention also encompasses closed circle oligonucleotides formed by the processes of the invention.

The closed circular oligonucleotides formed by the processes of the invention find a variety of uses, especially as templates for rolling circle amplification (RCA). Thus, the present invention also relates to a process for amplifying a selected oligonucleotide sequence comprising rolling circle amplification (RCA) using an amplification target circle (ATC) formed by the processes disclosed herein.

In accordance with the invention, linear 5'-phosphorothioates can be readily prepared by any of a variety of procedures known for making DNA and RNA oligonucleotides, either enzymatic or chemical, including automated solid phase DNA synthesis methods. Also in accordance with the present invention, 5'-thiophosphorylation can be carried out in excellent yields by automated solid phase DNA synthesis as well as by enzymatic methods known in the art.

The linear oligonucleotides used in practicing the processes of the invention are easily purified by polyacrylamide gel electrophoresis, exonuclease treatment, or by any number of chromatographic methods, including gel filtration chromatography and high performance liquid chromatography. To confirm a nucleotide sequence, oligonucleotides can be subjected to RNA and DNA sequencing by known procedures. Sequences of short oligonucleotides can also be analyzed by any known MALDI-TOF and electrospray mass spectroscopy method as reported by Wu, K. J et. al., in Rapid. Commun. Masss Spectrom. 1993, 4, pages 99–102.

The present invention relates to the synthesis, by chemical or enzymatic means, of DNA circles, especially single stranded circles, for example an 80-mer DNA circle, containing a single phosphorothioate as a replacement for a non-bridging oxygen atom at the site of ligation (see FIG. 21). Extension of this approach to the synthesis of phosphorothioate linked circular DNA by non-enzymatic ligation was also demonstrated. In addition, the present invention provides useful processes that mimic an enzymatic ligation reaction but are non-enzymatic in nature. The method of the invention is highly advantageous in that it is efficient, low cost and amenable for large-scale ligation of DNA and modified DNA analogs thereof, for use as probes, diagnostic agents, and therapeutic agents.

Figure 12:
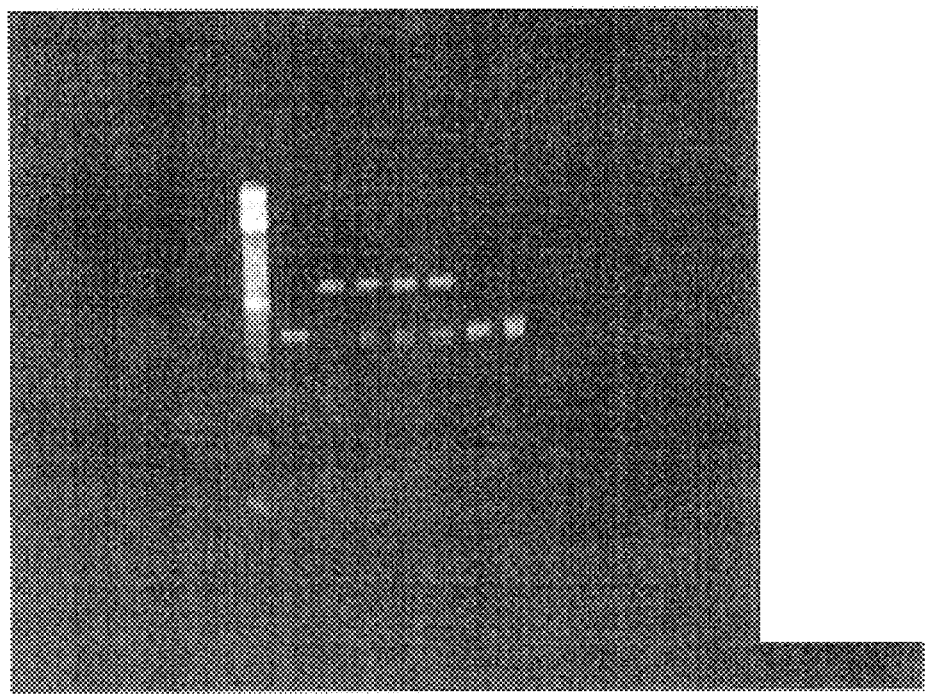
FIG. 12 shows a 15% TBE-Urea Ready PAGE gel analysis of T-4 DNA ligase catalyzed ligation reaction: Lanes from left to right are: (1). 10 bp marker from Gibo-BRL; (2). 5'-Phosphorothioate 80 mer open circle oligo (SEQ ID NO: 19) (3). Enzymatic reference circle; (SEQ ID NO: 23). 5'-Phosphate 80-mer open circle oligo (SEQ ID NO: 18) ligation reaction product with T-4 DNA ligase; (5). 5'-Phosphorothioate 80 mer open circle DNA (SEQ ID NO: 19) ligation reaction with T4 DNA ligase after 1 hour; (6). 5'-Phosphorothioate 80mer open circle DNA (SEQ ID NO: 19) ligation reaction with T4 DNA ligase after 2 hours; (7). No bridge oligo (SEQ ID NO: 22) ligation with 5'-phosphorothioate open circle oligo (SEQ ID NO: 19); (8). No enzyme ligation with 5'-phosphorothioate open circle oligo (SEQ ID NO: 19).
Figure 13:
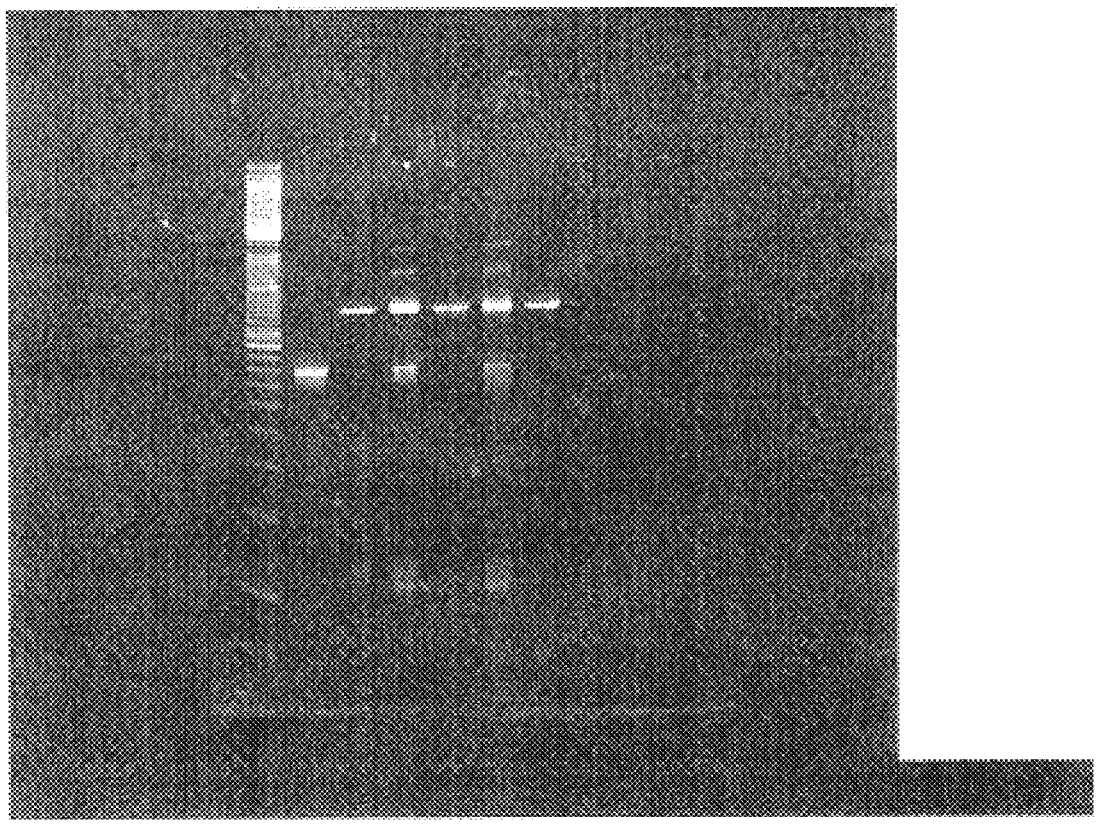
FIG. 13 shows a 15% TBE-Urea PAGE analysis of Exonuclease 1 and T-7 gene 6 Exonuclease Reaction: Lanes from left to right are: (1). 10 bp DNA ladder from Gibco-BRL; (2). 5'-Phosphorothioate open circle oligo (SEQ ID NO: 19) and 1 µl of 0.5 M DTT; (3). Enzymatic reference circle (SEQ ID NO: 24); (4). 5'-Phosphate open oligo (SEQ ID NO: 18) ligation reaction product in the absence of exonuclease treatment, (5). 5'-Phosphate open oligo (SEQ ID NO: 18) ligase reaction product in the presence of exonucleases, (6). 5'-Phophorothioate open oligo (SEQ ID NO: 19) ligation reaction product in the absence of exonuclease treatment, (7). 5'-Phophorothioate open oligo (SEQ ID NO: 19) ligation reaction product in the presence of exonuclease.

In one embodiment, the method of the invention forms an ATP dependent 3'-5' phosphorothioate linkage between the 3'-hydroxyl and 5'-phosphorothioate group of a single stranded DNA by T4 DNA ligase in presence of a 28-mer DNA bridge (FIG. 12). There, the reactions were carried out by hybridizing 10 $\mu$M of linear 5'-phosphorothioate and 12 $\mu$M of template strand. Simple qualitative inspection of gels for 1 hour and 2-hour time points indicate significant amounts of ligation in all cases. Comparison of 5'-phosphorothioate (lanes 5, and 6) with 5'-phosphate (lane 4) indicates 5'-phosphorothioate is a good substrate and similar to 5'-phosphate. Circularity of oligomers was confirmed by the treatment of purified circular DNA with exonuclease I and T7 gene 6 exonuclease (FIG. 13). In case of 5'-phosphorothioates a disulfide can be obtained by oxidative dimerization as reported by Gryaznov, S. M and Letsinger, R. L, Nucleic Acids Research, 21 (6), pages 1403–1408 (1993). However, treatment of 5'-phosphorothioate OCO with DTT during purification or inclusion of DTT in the reaction removed possibility of disulfide formation.

Figure 14:
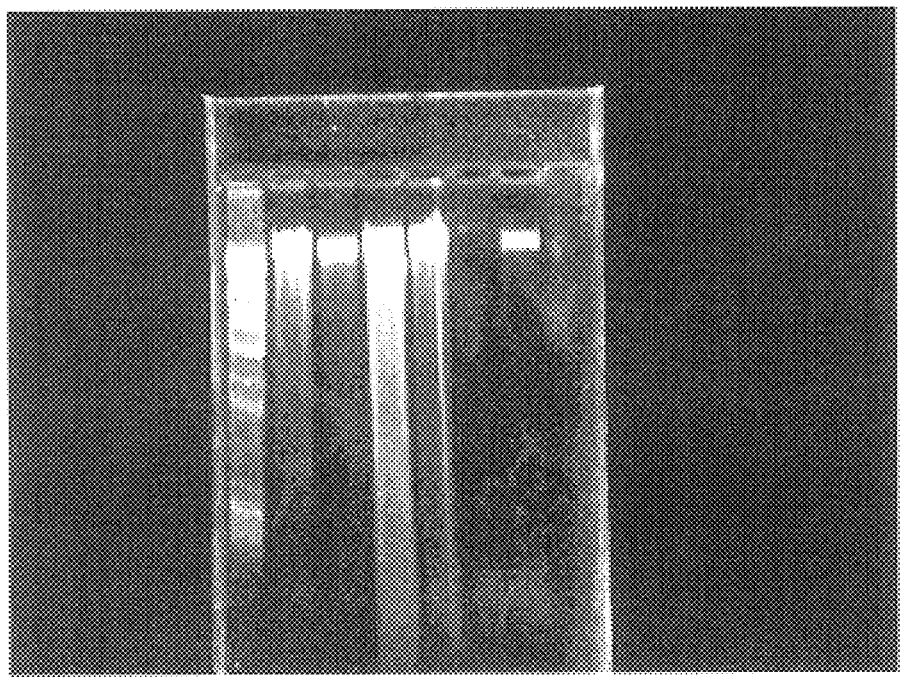
FIG. 14 shows a 0.8% Alkaline agarose gel analysis of RCA products obtained using Phage φ-29 DNA polymerase Rolling Circle Amplification (RCA) reaction: The lanes marked from left to right are: (1). Hind-III marker; (2). Enzymatic reference circle (SEQ ID 24) (; (3). Enzymatic phosphorothioate reference circle (SEQ ID NO: 25); (4). Chemically ligated Phosphate reference circle (SEQ ID NO.

The ability of phosphorothioate circles to serve as a template similar to a conventional phosphate circle is provided by the rolling circle amplification reaction (see FIG. 14). Qualitative analysis of PS (phosphorothioate) circle (lane 3) with phosphate circle (lane 2) shows that the phosphorothioate circles can serve as an efficient template. The efficiency of RCA (FIGS. 14 and 15) demonstrates for the first time that phosphorothioate circle replicates faithfully in the presence of DNA polymerases without any significant pause or lag. The efficiency of non-enzymatic circular DNA (lanes 4 and 5 in FIG. 14) in RCA reaction is very similar to enzymatic circles. Further proof that the efficiency of PS circle is similar to phosphate circle is provided by the incorporation of [$P^{32}$] dCTP in RCA reaction (see FIG. 16)

The enzymatic and non-enzymatic ligation of 5'-phosphorothioates is considerably less well studied as a mechanistic probe. However, a number of chemical ligation methods that lead to the formation of a 5'-S-thioester linkage in which the sulfur is located at the 5'-bridging region have been reported in the literature. All the known non-enzymatic methods to date have been based on the reaction of 3'-phosphorothioates with a leaving group such as iodo, bromo or tosyl groups at 5'-end to generate either a circular or a ligated DNA. Reaction of 5'-phosphorothioates (OCO) in the presence of short template oligo (BO) under non-enzymatic conditions with a water-soluble N-ethyl-N'-(dimethylaminopropyl)-carbodiimide hydrochloride (EDC), gave circular DNA in good yield. Simple qualitative inspection of gels after 1 hour indicates significant amounts of ligation in all cases (see FIG. 17). Comparison of 5'-phosphorothioate (lane 5) with 5'-phosphate (lane 4) indicates 5'-phosphorothioate is a good substrate similar to 5'-phosphate. The properties of non-enzymatic circles obtained with EDC are very similar to enzymatic ligation DNA circle. In addition, the effect of ATP on non-enzymatic circle synthesis was also investigated (see FIG. 18). Mimicking enzymatic ligation under non-enzymatic conditions should provide additional structure elements that will play an important role both in both enzymatic and non-enzymatic conditions. Addition of ATP to non-enzymatic ligation reaction in general should provide intermediates similar to enzymatic ligation by phosphate exchange that occurs in natural capases.

The invention described herein provides a novel enzymatic or chemical ligation of 5'-phosphorothioates as well as 5'-phosphates on a complementary template strand. The new method forms a phosphorothioate diester between 3'-hydroxyl and 5'-phosphorothioate or a phosphodiester with 5'-phosphate. The ligation methods of the present invention have been applied to the synthesis of a single stranded 80-mer circular DNA using both enzymatic and chemical ligation approaches. The efficiency of 5'-phosphorothioate directed ligation by chemical and T4 DNA ligase catalyzed approach is very similar to that of enzymatic 5'-phosphate ligation reaction. The data also show that 5'-phosphorothioate is an excellent substrate for T4 DNA ligase. The phosphorothioate and phosphate containing circular DNA synthesized by both chemical and enzymatic methods undergo rolling circle amplification (RCA) reaction with φ-29 DNA polymerase. Exonuclease cleavage resistance and gel mobility studies provide further evidence supporting formation of circular DNA. Evidence is also provided for the rolling circle amplification of chemically ligated Circle 1 (see Table 1) by radio labeled [$P^{32}$] dCMP incorporation into RCA product. The fact that a single phosphorothioate residue in the Circle 1 did not cause significant pause to rolling circle amplification suggests that phosphorothioate ligation is a significant alternative to conventional ligation dependent amplification of nucleic acids.

In carrying out rolling circle amplification (RCA) using the oligonucleotide circles formed by the methods disclosed herein, such circles serve as templates for the amplification process. Amplification target circles (ATC) useful in the processes of the present invention are circular single-stranded DNA molecules, generally containing between 40 to 1000 nucleotides, preferably between about 50 to 150 nucleotides, and most preferably between about 50 to 100 nucleotides. The ATCs useful in the processes disclosed herein may have functionally different portions, or segments, making them particularly useful for different purposes. At least one such portion will be complementary to one or more oligonucleotide primers. Thus, all types of ATCs as disclosed herein can be formed by the methods of the invention and will differ from conventional ATCs as disclosed elsewhere only in that the ATCs formed by the methods of the present invention will have at least one phosphorothioate linkage, which linkage does not adversely affect the utility of said ATCs in serving as templates for rolling circle amplifications.

For ATCs useful in the processes disclosed herein, the primer complement portion is a required element of an amplification target circle. Other portions are optional and can be selected to have an arbitrarily determined sequence. It is preferred that ATCs do not have any sequences that are self-complementary, a condition met if there are no complementary regions greater than about six nucleotides long without a mismatch or gap. ATCs useful in the process have been described in Lizardi, U.S. Pat. No. 5,854,033 (the disclosure of which is hereby incorporated by reference in its entirety) and in Lizardi et al, Mutation Detection and Single-Molecule Counting Using Isothermal Rolling Circle Amplification, *Nature Genetics*, 19, 225–232 (1998).

Figure 1:
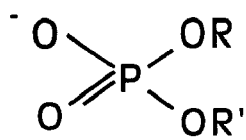
FIG. 1 shows the structures of phosphorothioates as isosteres of phosphates.
Figure 1:
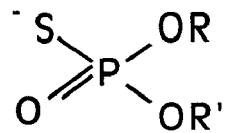
Figure 1:
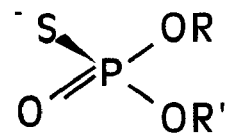
Figure 1:
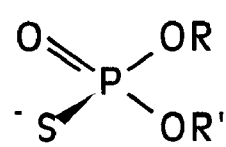

The success of 5'-phosphorothioate directed-ligation in probing specific sequences of DNA arises in large part from high enzymatic selectivity against diastereomeric phosphorothioates (see FIG. 1) at the ligation junction. The enhanced ability of diastereomeric selectivity of DNA ligases allows probing of single base mismatches at either side of the ligation junction (as well as a few nucleotides removed therefrom) within one of the oligonucleotide binding sites.

Addition of ATP to a chemical ligation reaction seems to improve the circle synthesis. The present method also provides evidence that enzymatic ligation can also be achieved with 5'-phosphorothioate independent of $Mg^{2+}$ in the ligation reaction. However, chemical ligation reaction is found to be non-discriminatory towards different metal ions.

Any DNA ligase that readily forms a 3'-5' phosphorothioate is suitable for this ligation method. Preferred ligases are those that preferentially form phosphorothioate bonds at nicks in double-stranded DNA. Thermostable ligases are especially preferred. Many suitable ligases are known, such as T 4 DNA ligase, *E.coli* DNA ligase, Taq DNA ligase, Tth DNA ligase, *Thermus scotoductus* DNA ligase, *Rhodothermus marinus* DNA ligase, Ampligase, Bst ligase, T4 RNA ligase and cappases. An example of 5'-phosphorothioate directed ligation using T4 DNA ligase has been described in the experimental section (see FIG. 4).

Preferably, the method of forming the circular oligonucleotide template involves adapter directed coupling. Methods such as this are described in FIG. 21. This method includes, generally, the steps: hybridizing a linear precursor having two ends to an adapter, i.e., positioning oligonucleotide, to form an open oligonucleotide circle; joining two ends of open circle oligonucleotides circle to form the circular template; and recovering the single-stranded circular oligonucleotide template. The positioning oligonucleotide is complementary to the two opposite ends of linear precursor. In one embodiment of the present invention, the precursor and adaptor are mixed and annealed, thereby forming a complex in which 3' and 5' ends of the precircle are adjacent. The adapter juxtaposes the two ends. This occurs preferentially under high dilution i.e. no greater than about 100 micromolar, by using very dilute concentrations of adapter and precursor oligomers or by slow addition of adapter to the reaction mixture. These ends then undergo coupling by T 4 DNA ligase forming 3'-5' phosphorothioate linkage-containing circle. The resulting circular template can be purified by standard polyacrylamide gel electrophoresis.

The phosphorothioate directed ligation could readily be applied to the synthesis of dumbbells, padlocks and hairpins. The phosphorothioate ligation can also be applied to sticky-ended hairpins giving rise to a dumbbell or a large circle by using known methods in the literature.

Significant structural and mechanistic features of 5'-phosphorothioate directed ligation reaction and its application to single nucleotide polymorphisms include the following.

Figure 2:
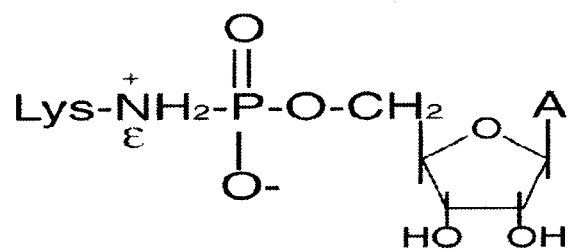
FIG. 2 shows a schematic of several DNA ligation mechanisms.

The enzymatic ligation of 5'-phosphorothioates is considerably less well studied as a mechanistic probe. However, a number of chemical ligation methods that lead to the formation of a 5'-S-thioester linkage in which the sulfur is located at the 5'-bridging region have been reported in the literature (17–30). Replacement of any of two non-bridging oxygens attached to the inter-nucleotide phosphorous atom by sulfur creates, by virtue of asymmetry, new center(s) of chirality and results in the formation oligonucleotide diastereomers. The chirality at the phosphorus is designated as Rp and Sp. In addition, introduction of a sulfur atom in the internucleotide phosphorothioate results in increased bond length, reduced hydration, reduced electronegativity and altered metal ion affinity. In general, the enzymatic ligation with 5'-phosphate donor group occurs via a minimal three-step mechanism as outlined in FIG. 2. In the first step, the ligase reacts with ATP to form an adenyllylated enzyme with release of inorganic phosphate. In the second step, the adenylyl group is transferred from the enzyme to the 5'-phosphate group of the donor to form an adenylylated molecule having a 5'-5'-phosphoroanhydride bond. The third step involves reaction of the 3'-hydroxyl group of the acceptor with the activated 5'-phosphoryl group of the donor, resulting in the formation of a phosphodiester linkage with the concomitant release of AMP (see FIGS. 2 and 3A).

FIG. 3B shows the mechanism of Phosphorothioate enzymatic ligation. This last step may proceed mechanistically through a direct nucleophilic displacement. Enzymatic ligations are commonly most selective at the ligation junction, a fact that is attributed to the precise geometric control that the enzyme takes in orienting the reactive groups for in-line attack at phosphorus. Since the chiral orientation is an important factor which influences duplex structure, enzyme recognition, conformation and/or hybridization kinetics, it is anticipated that the introduction of sulfur may have significant effect on any of the steps of the ligation as well.

The present invention has several applications similar to the conventional ligation reaction and represents a rational alternative ligation method that can be applied to circular DNA synthesis and as a general technique in molecular biology. The phosphorothioate circular DNA produced by the present invention can be used in the rolling circle amplification that has several significant uses as described by Lizardi (see U.S. Pat. No. 5,854,033, 1998). In addition, the phosphorothioate directed ligation produces circular DNA that is more stable to exo- and endonucleases. Such circular DNA serve as excellent tools for investigation of nucleic acid-protein interactions, further conjugation and detection probe systems in DNA based diagnostics.

In one aspect, the present invention relates to a means of detecting the presence of a mutation in an oligonucleotide, or polynucleotide, sequence. Such mutations result in mismatches when such an oligonucleotide is paired with an otherwise complementary nucleotide sequence present in another oligonucleotide, such as a probe oligonucleotide. Where such mutation is a point mutation, the result is a single nucleotide polymorphism (SNP) which can be detected using the processes disclosed herein.

In accordance with the foregoing, the present invention relates to a process for detecting nucleotide mismatches comprising:

contacting a first oligonucleotide, comprising first and second segments, with a second oligonucleotide wherein said second oligonucleotide comprises a first complementary segment, a second complementary segment, and a third segment and wherein said second oligonucleotide also comprises a thio phosphate at its 5'-terminus, and wherein said first and second complementary segments of said second oligonucleotide are complementary to the first and second segments of said first oligonucleotide one of which first oligonucleotide segments comprises at least one mismatched nucleotide, and wherein said third segment is not complementary to said first oligonucleotide, and wherein said contacting occurs under conditions promoting hybridization of said first and second segments with said first and second complementary segments, and wherein said hybridization results in the formation of a complex in which the 5'- and 3'-ends of said second oligonucleotide are adjacent to each other, and said 3'-nucleotide may be opposite a mismatched nucleotide of said first oligonucleotide, contacting said hybridized complex with a ligation catalyst under conditions promoting ligation of the 5'- and 3'-ends of said second oligonucleotide in said hybridized complex when said mismatch is not present, and detecting formation of ligated second oligonucleotide wherein reduced or non-formation thereof indicates the presence of a nucleotide mismatch.

Of course, the structure of said third segment are optional and may be chosen so as to best combine with a rolling circle amplification primer.

In a preferred embodiment of this process, the catalyst is an enzyme, most preferably Ampligase or T4 DNA or RNA ligase.

In the first step of enzymatic ligation, ligase will react with ATP via lysine in the enzyme active site to form an adenylated enzyme intermediate with the release of inorganic pyrophosphate. In the second step, the adenyl group from enzyme-ATP complex is transferred to 5'-phosphate donor group resulting in the formation of a labile 5'-5'-phosphoroanhydride. In the third step, the 3'-hydroxyl group of the acceptor will react with the 5'-5'-phosphoanhydride intermediate resulting in the formation of a new 3'-5'-phosphodiester bond with the concomitant release of AMP. This last step may proceed mechanistically through a direct nucleophilic substitution. (See, for example, FIG. 3)

Enzymatic ligations in general are more selective at the ligation junction, possibly due to more precise control of geometry that the enzyme takes in orienting the reactive groups for in-line attack at phosphorus. Since the chiral and physico-chemical properties of phosphorothioate plays an important role that influence duplex structure, enzyme recognition, conformation and hybridization kinetics, it is anticipated that the introduction of sulfur may have significant effect on any of the steps of ligation as well. In addition, it is postulated that only one of the diastereomer should serve as a substrate to DNA ligation resulting in homochiral phosphorothioate bond formation. (See, for example, FIG. 2)

Diastereo-selective synthesis of phosphorothioates remains a great synthetic challenge to the chemists working in antisense therapeutics and nucleic acids based diagnostics. It is possible that oligomers having diastereomerically enriched phosphorothioate linkages could possess advantages in hybridizing to a target mRNA in antisense based DNA therapeutics. There are several reports in the literature that uses 1-thiotriphosphates of A, T, G and C in presence of specific DNA polymerases to produce chiral phosphorothioates. However, enzymatic ligation that produces stereoselective phosphorothioate is less well studied. Bryant and Benkovic (Biochemistry (1982) 21, 5877–5885) have investigated stereochemical details of the T4 RNA ligase reaction mechanism by examining the reactivity of phosphorothioate analogues in the adenosine 5'-triphosphate (ATP) dependent and ATP-independent RNA ligase reactions. Only the Sp isomer of the diastereomeric inosine 5'-α-thiodiphospho-5'-adenosine [App(s)I], was active as an activated donor substrate in the ATP-independent RNA ligase reaction. The thiophosphodiester linkage in the ligation product, ApApAp (s)I, that is formed by the reaction of App(s)I (Sp) with the oligonucleotide acceptor ApApA, was shown to have the Rp configuration. This indicated that phosphodiester bond formation occurs by a direct, nucleophilic displacement of AMP from App(s)I by the 3'-hydroxyl group of ApApA with inversion of configuration at phosphorous. The adenylated intermediate, App(s)Ap, that is formed from the phosphorothioate donor, p(s)Ap, in the ATP-dependent RNA ligase reaction was shown to have the same stereochemical configuration as is required for the ATP-independent RNA ligase reaction. These results indicate that RNA ligase maintains a preferred chirality at phosphorus through the adenylation and ligation steps of the reaction mechnism. An unusual result is the accumulation of adenosine cyclic 2',3'-phosphate 5'-phosphorothioate in the ATP-dependent RNA ligase reaction employing the donor p(s)Ap when the acceptor ApApA. This observation suggests that there are two distinct but reactive modes for donor molecules.

Some aspects of the use of enzymatic methods to synthesize oligonucleotides having chiral phosphorothioate linkages have been investigated. Burgers, P. M. J. and Eckstein, F. (1979), J. Biological Chemistry, 254:6889; and Gupta, A., DeBrosse, C., and Benkovic, S. J. (1982) J. Biol. Chem., 256:7689 enzymatically synthesized diastereomerically pure polydeoxy-adenylic acid having phosphorothioate linkages. Brody, R. S. and Frey, P. S. (1981), Biochemistry, 20: 1245; Eckstein, F. and Jovin, T. M (1983), Biochemistry, 2: 4546, Brody, R. S., Adler, S., Modrich, P., Stec, W. J., Leznikowski, Z. J., and Frey, P. A. (1982) Biochemistry, 21: 2570–2572; and Romaniuk, P. J. and Eckstein, F. (1982) J. Biol. Chem., 257: 7684–7688 all enzymatic ally synthesized poly TpA and poloy ApT phosphorothioates while Burgers, P. M. J. and Eckstein, F. (1978) Proc. Natl. Acad. Sci. USA, 75: 4798–4800 enzymatically synthesized poly UpA phosphorothioates. Cruse, W. B. T., Salisbury, T., Brown, T., Cosstick, R. Eckstein, F., and Kennar, O. (1986), J. Mol. Biol., 192: 891, linked three diastereomeric RpGpC phosphorothioate dimers via natural phosphodiester bonds into a hexamer. Most recently Ueda, T., Tohda, H., Chikazuni, N., Eckstein, R., and Watanabe, K. (1991) Nucleic Acids Research, 19: 547, enzymatically synthesized RNAs having from several hundred to ten thousand nucleotides incorporating Rp linkages of high diastereomeric excess.

The present invention of 5'-thio phosphate directed enzymatic DNA ligation is designed to identify a single nucleotide polymorphism site. The invention is further directed to methods of using such information in genetic analysis using rolling circle amplification of ligated product. A major problem facing conventional 5'-phosphate directed ligation approach is mismatch ligation that results mainly due to non-Watson/Crick hybridization events. For example nucleotide mismatches such as G/T, G/A and G/G were known to misligate very effectively by several DNA ligases. Though varying stringency of hybridization conditions by several reported techniques in the literature will help to reduce mismatch ligation, however it is not possible to eliminate mismatch ligation completely. In this context, it is postulated that the use of 5'-thio phosphates instead of conventional 5'-phosphates should yield highly specific ligation without any mismatch ligation. As disclosed herein, 5'-thio phosphates will function as a structural mimic, which will favor stereo-selective ligation with correct base pair. In addition to specificity that often has been achieved through Watson-Crick hybridization, in the case of 5'-thio phosphate directed enzymatic ligation proper orientation of right diastereomer of 5'-thio phosphate also plays a very important role in diastereo-selective ligation. As discussed above, stereo selectivity of 5'-thio phosphates is controlled by either of three major steps involved in enzymatic ligation.

As used herein, the terms "portion," "segment," and "fragment," when used in relation to polynucleotides or oligonucleotides of any kind, including the hairpin oligonucleotides described herein, refer to a continuous sequence of nucleotide residues, which sequence forms a subset of a larger sequence. For example, if a polynucleotide were subjected to treatment with any of the common endonucleases, the oligonucleotides resulting from such treatment would represent portions, segments or fragments of the starting polynucleotide(s).

In a further embodiment of the present invention, the processes disclosed herein further comprise detecting the occurrence of ligated second oligonucleotide by contacting the third segment of ligated second oligonucleotide with a primer oligonucleotide complementary to said third segment under conditions promoting hybridization of said primer to said third segment and further contacting said complex with a rolling circle amplification (RCA) enzyme under conditions promoting rolling circle amplification of said ligated second oligonucleotide. Thus, where a mutation is present in the target oligonucleotide and said mutation is opposite, for example, the 3'-nucleotide of the OCO (or OCP), the ligation enzyme, such T4 DNA ligase, will fail to ligate the OCO so that no circle is formed and no rolling circle amplification results when an RCA-promoting enzyme is added along with the primer complementary to the third segment of the OCP. However, where no such mutation occurs (i.e., where there is no mismatch) the enzyme forms a circular product and addition of an RCA primer and RCA-promoting enzyme results in amplification on the circular template to form tandem sequence DNA (TS-DNA) which can be readily detected using probes specific for sequences therein as well as where the nucleoside triphosphates used to form said TS-DNA is itself labeled, such as with a radiolabel or some type of chromogenic label, such as a fluorescent label.

Such applications allow quantitative determination of the extent of amplification occurring and/or the amount of TS-DNA being formed or, in some circumstances, to be able to measure in a discriminating fashion the relative quantities of amplification target circles (ATCs) being formed (the circular products of ligation). The present invention works well with any number of standard detection schemes, such as where special deoxynucleoside triphosphates (dNTPs) are utilized that make it easier to do quantitative measurements. The most common example is where such nucleotide substrates are radiolabeled or have attached thereto some other type of label, such as a fluorescent label or the like. Again, the methods that can be employed in such circumstances are many and the techniques involved are standard and well known to those skilled in the art. Thus, such detection labels include any molecule that can be associated with amplified nucleic acid, directly or indirectly, and which results in a measurable, detectable signal, either directly or indirectly. Many such labels for incorporation into nucleic acids or coupling to nucleic acid probes are known to those of skill in the art. General examples include radioactive isotopes, fluorescent molecules, phosphorescent molecules, enzymes, antibodies, and ligands.

Examples of suitable fluorescent labels include CyDyes such as Cy2, Cy3, Cy3.5, Cy5, and Cy5.5, available from Amersham Pharmacia Biotech. Further examples of suitable fluorescent labels include fluorescein, 5,6-carboxymethyl fluorescein, Texas red, nitrobenz-2-oxa-1,3-diazol-4-yl (NBD), coumarin, dansyl chloride, and rhodamine. Preferred fluorescent labels are fluorescein (5-carboxyfluorescein-N-hydroxysuccinimide ester) and rhodamine (5,6-tetramethyl rhodamine). These can be obtained from a variety of commercial sources, including Molecular Probes, Eugene, Oreg. and Research Organics, Cleveland, Ohio.

Labeled nucleotides are a preferred form of detection label since they can be directly incorporated into the products of RCA during synthesis. Examples of detection labels that can be incorporated into amplified DNA include nucleotide analogs such as BrdUrd (Hoy and Schimke, *Mutation Research*, 290:217–230 (1993)), BrUTP (Wansick et al., *J. Cell Biology*, 122:283–293 (1993)) and nucleotides modified with biotin (Langer et al., *Proc. Natl. Acad. Sci. USA*, 78:6633 (1981)) or with suitable haptens such as digoxygenin (Kerkhof, *Anal. Biochem.*, 205:359–364 (1992)). Suitable fluorescence-labeled nucleotides are Fluorescein-isothiocyanate-dUTP, Cyanine-3-dUTP and Cyanine-5-dUTP (Yu et al., *Nucleic Acids Res.*, 22:3226–3232 (1994)). A preferred nucleotide analog detection label for DNA is BrdUrd (BUDR triphosphate, Sigma), and a preferred nucleotide analog detection label is Biotin-16-uridine-5'-triphosphate (Biotin-16-dUTP, Boehringher Mannheim). Radiolabels are especially useful for the amplification methods disclosed herein.

In a preferred embodiment, said rolling circle amplification is exponential rolling circle amplification (ERCA) and the RCA enzyme is a member selected from the group consisting of *E. coli* DNA polymerase 1, Klenow fragment, T4 or T7 DNA polymerases, Phi 29 DNA polymerase and Taq polymerase. Where the RCA is ERCA, the prefered enzyme is Phi 29 DNA polymerase. In a preferred embodiment of such processes, the first oligonucleotide is part of a genomic DNA, or is derived from genomic DNA or is itself a genomic DNA.

In one embodiment, the OCO, or open circle probe (OCP), or second oligonucleotide, as disclosed in the processes herein, can include a hairpin oligonucleotide. In one such embodiment, the hairpin oligonucleotide comprises a 5'-thiophosphate group, a 5 to 10 base stem portion, a 10 to 20 base loop, and a 10 to 50 nucleotide 3'-arm. Such a hairpin thereby acts as a suicide probe to eliminate false priming in any subsequent ERCA steps.

The present invention also contemplates embodiments wherein an OCO or second oligonucleotide contains internal phosphorothioates, preferably between 2 and 5 phosphorothioates, in addition to the 5'-thiophosphate. Such a modification, especially at the 3'-portion of the OCO or OCP, facilitates exonuclease resistance thereby providing a stable rolling circle amplification (RCA) probe for use in cell and tissue based ligations.

In accordance with the present invention, a target oligonucleotide may be attached to a solid support, preferably glass or plastic. Attachment of oligonucleotides to such supports can be either directly or through means of some molecular species, such as some type of polymer, biological or otherwise, that serves to attach said primer or ATC to a solid support. Such solid-state substrates useful in the methods of the invention can include any solid material to which oligonucleotides can be coupled. This includes materials such as acrylamide, cellulose, nitrocellulose, glass, polystyrene, polyethylene vinyl acetate, polypropylene, polymethacrylate, polyethylene, polyethylene oxide, glass, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids. Solid-state substrates can have any useful form including thin films or membranes, beads, bottles, dishes, fibers, woven fibers, shaped polymers, particles and microparticles. A preferred form for a solid-state substrate is a glass slide or a microtiter dish (for example, the standard 96-well dish). Preferred embodiments utilize glass or plastic as the support. For additional arrangements, see those described in U.S. Pat. No. 5,854,033.

Methods for immobilization of oligonucleotides to solid-state substrates are well established. Oligonucleotides, including address probes and detection probes, can be coupled to substrates using established coupling methods. For example, suitable attachment methods are described by Pease et al., *Proc. Natl. Acad. Sci. USA* 91(11):5022–5026 (1994). A preferred method of attaching oligonucleotides to solid-state substrates is described by Guo et al., *Nucleic Acids Res.* 22:5456–5465 (1994).

Oligonucleotide primers useful in the present invention can be synthesized using established oligonucleotide synthesis methods. Methods of synthesizing oligonucleotides are well known in the art. Such methods can range from standard enzymatic digestion followed by nucleotide fragment isolation (see for example, Sambrook, et al., *Molecular Cloning: A Laboratory Manual*, Second Edition, Cold Spring Harbor, N.Y., (1989), Wu et al, *Methods in Gene Biotechnology* (CRC Press, New York, N.Y., 1997), and *Recombinant Gene Expression Protocols*, in *Methods in Molecular Biology*, Vol. 62, (Tuan, ed., Humana Press, Totowa, N.J., 1997), the disclosures of which are hereby incorporated by reference) to purely synthetic methods, for example, by the cyanoethyl phosphoramidite method using a Milligen or Beckman System 1 Plus DNA synthesizer (for example, Model 8700 automated synthesizer of Milligen-Biosearch, Burlington, Mass. or ABI Model 380B). Synthetic methods useful for making oligonucleotides are also described by Ikuta et al., *Ann. Rev. Biochem.* 53:323–356 (1984), (phosphotriester and phosphite-triester methods), and Narang et al., *Methods Enzymol.*, 65:610–620 (1980), (phosphotriester method). Protein nucleic acid molecules can be made using known methods such as those described by Nielsen et al., *Bioconjug. Chem.* 5:3–7 (1994).

Methods for the synthesis of primers containing exonuclease-resistant phosphorothioate diesters by chemical sulfurization are well-established. The solid phase synthesis of random primers employs one or several specifically placed internucleotide phosphorothioate diesters at the 3'-end. Phosphorothioate triesters can be introduced by oxidizing the intermediate phosphite triester obtained during phosphoramidite chemistry with 3H-1,2-benzodithiol-3-one 1,1 dioxide[1,2] or Beaucage reagent to generate pentavalent phosphorous in which the phosphorothioate triester exists as a thione. The thione formed in this manner is stable to the subsequent oxidation steps necessary to generate internucleotidic phosphodiesters. (lyer, R. P., Egan, W., Regan, J. B., and Beaucage, S. L. J. Am. Chem. Soc., 112: 1253 (1990), and lyer, R. P., Philips, L. R., Egan, W., Regan, J. B., and Beaucage, S. L. J. Org. Chem., 55: 4693 (1990))

Many of the oligonucleotides described herein are designed to be complementary to certain portions of other oligonucleotides or nucleic acids such that hybrids can be formed between them. The stability of these hybrids can be calculated using known methods such as those described in Lesnick and Freier, *Biochemistry* 34:10807–10815 (1995), McGraw et al., *Biotechniques* 8:674–678 (1990), and Rychlik et al., *Nucleic Acids Res.* 18:6409–6412 (1990).

DNA polymerases useful in the rolling circle replication step of RCA must perform rolling circle replication of primed single-stranded circles (or each strand of a duplex substrate). Such polymerases are referred to herein as rolling circle DNA polymerases. For rolling circle replication, it is preferred that a DNA polymerase be capable of displacing the strand complementary to the template strand, termed strand displacement, and lack a 5' to 3' exonuclease activity. Strand displacement is necessary to result in synthesis of multiple tandem copies of the ATC. A 5' to 3' exonuclease activity, if present, might result in the destruction of the synthesized strand. It is also preferred that DNA polymerases for use in the disclosed method are highly processive. The suitability of a DNA polymerase for use in the disclosed method can be readily determined by assessing its ability to carry out rolling circle replication. Preferred rolling circle DNA polymerases are bacteriophage φ29 DNA polymerase (U.S. Pat. Nos. 5,198,543 and 5,001,050 to Blanco et al.), phage M2 DNA polymerase (Matsumoto et al., Gene 84:247 (1989)), phage PRD1 DNA polymerase (Jung et al., *Proc. Natl. Acad. Sci. USA* 84:8287 (1987), and Zhu and Ito, *Biochim. Biophys. Acta.* 1219:267–276 (1994)), VENT.RTM. DNA polymerase (Kong et al., *J. Biol. Chem.* 268:1965–1975 (1993)), Klenow fragment of DNA polymerase I (Jacobsen et al., *Eur. J. Biochem.* 45:623–627 (1974)), T5 DNA polymerase (Chatterjee et al., *Gene* 97:13–19 (1991)), and T4 DNA polymerase holoenzyme (Kaboord and Benkovic, *Curr. Biol.* 5:149–157 (1995)). φ-29 DNA polymerase is most preferred. Equally preferred polymerases include T7 native polymerase, *Bacillus stearothermophilus* (Bst) DNA polymerase, *Thermoanaerobacter thermohydrosulfuricus* (Tts) DNA polymerase (U.S. Pat. No. 5,744,312), and the DNA polymerases of *Thermus aquaticus*, *Thermus flavus* or *Thermus thermophilus*. Equally preferred are the φ29-type DNA polymerases, which are chosen from the DNA polymerases of phages: φ29, Cp-1, PRD1, φ15, φ21, PZE, PZA, Nf, M2Y, B103, SF5, GA-1, Cp-5, Cp-7, PR4, PR5, PR722, and L17. In a specific embodiment, the DNA polymerase is bacteriophage φ29 DNA polymerase wherein the multiple primers are resistant to exonuclease activity and the target DNA is high molecular weight linear DNA.

The ability of a polymerase to carry out rolling circle replication can be determined by using the polymerase in a rolling circle replication assay such as those described in Fire and Xu, *Proc. Natl. Acad. Sci. USA* 92:4641–4645 (1995) and in Lizardi (U.S. Pat. No. 5,854,033, e.g., Example 1 therein).

Single-stranded circular DNA has been found useful in many different areas of biotechnology, both of an experimental as well as commercial nature. One important such use is as a substrate for rolling circle DNA replication. In this procedure, a single-stranded circle of DNA is mixed with a short strand of single-stranded complementary primer DNA and the two separate strands are allowed to anneal. After addition of a DNA polymerase, such as the Klenow fragment, the intact circle is used as a template by the enzyme and then replicated from the 3'-end of the primer strand. After the enzyme has gone around the circular template, it encounters the 5'-end of the primer, which is then displaced from the template strand so that the enzyme continues to move around the circular template while a long, unbroken single strand of DNA is generated. Such single strand has been referred to as single-stranded concatenated DNA (Ruth and Driver, WO 92/01813). The single-stranded circular products of the present invention are ideally suited for use as a substrate in such processes. The product prepared by the method according to the present invention can ultimately yield single-strand concatenated DNA having numerous different sequential segments that can act as probes, detection sites or restriction sites for further processing.

Heretofore, the products of so-called "rolling circle amplification," or RCA, have been used as binding sequences for probes containing complementary sequences for specific sequences located in target DNA whose presence it was desired to detect. In essence, the result is to amplify sequences contained in the circular template to facilitate detection of sequences contained in a target.

In addition, RCA has been used (see Ruth and Driver, WO 92/01813) to produce concatenated single-stranded DNA containing repeated sequences complementary to those contained in the single-stranded circular substrates but containing restriction sites. Thus, when the concatenated DNA is treated with restriction enzymes, it is cut into short, repetitive segments which can, if desired, be ligated to form structures complementary to the original circles. With the addition of primers and DNA polymerase, such process can be repeated to form copies of the original circles. The present invention eliminates the need for such multistep processes by duplicating the desired circles at the outset, thus eliminating the need for a second round of RCA.

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

The present invention will now be further described by way of the following non-limiting examples. In applying the disclosure of these examples, it should be kept clearly in mind that other and different embodiments of the methods disclosed according to the present invention will no doubt suggest themselves to those of skill in the relevant art.

EXAMPLE 1

Ligation of 5'-Phosphorothioate Containing Linear Circle using T-4 DNA Ligase

To 100 μl of 1×T-4 DNA ligase buffer pH 7.8 (USB), containing 50 mM Tris.HCl, 10 mM $MgCl_2$, 10 mM DTT, 1.0 mM ATP, 25 μg of bovine serum albumin was added 10 μM of open circle oligo (OCO) and 12 μM of bridge oligo (BO). After heating to 60° C. for 30 min, the reaction mixture was allowed to cool down on an ice bath for additional 30 min. To this was added 15 μl of T4 DNA ligase (USB, 400 Units/μl) and incubated at 37° C. for 2 hours (final reaction volume was 1.0 ml). An aliquot (5 μl) of reaction mixture was taken for gel analysis at 1 hour and 2 hours. Place reaction sample at 90° C. on a heating block for two minutes and then on an ice-water bath. Remove 5 μl aliquot and place in labeled sterile microcentrifuge tube for gel analysis as shown in FIG. 12. The ligase reaction samples were frozen and then lyophilized. To the pellets thus obtained was added 10 μl of water and 20 μl of deionized formamide. Samples were heated at 90° C. for 2 minutes and then placed on an ice-water bath prior to loading onto 15% TBE-Urea polyacrylamide gel. Gels were visualized by short wave length UV shadowing at 254 nm. Cut out the lower migrating band and place in sterile siliconized 1.5 ml tube. Add 200 μl of 3.0M sodium acetate pH 5.2 and 800 μl of water. Vortex thoroughly. Fix the tube horizontally to the bottom of the 37° C. orbital shaker. Set the shaker to 256 rpm and elute the circle overnight.

The following day, equilibrate a PD10 column with 40 ml of water. Centrifuge the gel fragments for a few seconds to pellet the gel chunks. Remove supernatant and place in a new siliconized tube. When PD10 column is equilibriated, load elution sample onto column and allow sample to run into column. Add water a 500 μl increments until 2.5 ml have passed through the column. Collect the next four 1.0 ml fractions in siliconized tubes. Take 50 μl aliquots from each fraction. Read absorbance at 260 nm and 280 nm using 50 μl cuvette on a UV spectrophotometer. Scan peak fractions to record spectral profile. Calculate concentration of circle product using conversion 1 OD 260–33 μg/ml. Split aliquots and store at −20° C. degrees. Typical isolated yields are in the range of 40 to 44%.

The circular structure of products was confirmed by resistance to 3' exonuclease digestion and to 5' dephosphorylation under reaction conditions in which a linear precircle was completely destroyed or dephosphorylated. Accordingly, the 3' exonuclease activity of T4 DNA polymerase cleaved linear precircles, but not circular products. The slightly slower gel mobility of the circles relative to the precircles was consistent with the occurrence of circularization.

EXAMPLE 2

Exonuclease Treatment of Ligation Reaction Products

Place the ligation reactions from Example 1 after 2 hours at 90° C. on a heating block for two minutes and then place in ice-water bath. To this add 30 μl of 1.0 M glycine buffer (pH 9.5) 50 μl of Exonuclease I (USB, 10 Units/μl), and 10 μl of T7 gene 6 Exonuclease (USB, 50 Units/μl). The reaction mixture was incubated at 37° C. for 2 hours. Place reaction sample in 90° C. on a heating block for two minutes and then place in ice-water bath. Remove 5 μl of reaction mixture and analyze by 15% TBE-Urea Ready PAGE gel (Novex) as described in FIG. 13.

EXAMPLE 3

Rolling Circle Amplification of Circular DNA Products

The RCA reactions were carried out in 20 μl of total volume containing 50 nM circularized probes, 1 μM of rolling-circle primer, in 50 mM Tris.HCl pH 7.5, 10 mM MgCl$_2$, 20 mm ammonium sulfate, 1 mM each of dATP, dCTP, dGTP and dTTP, 5% glycerol, 4 ng/ml of yeast pyrophosphatase. Phage φ-29 DNA polymerase was added last at a concentration of 10 Units/μl (approximately 100 nM). The reactions were incubated at 37° C. for 20 hours. After 20 hours the reaction was stopped by the addition of 10 mM EDTA and the aliquots (5 μl) of the RCA reaction were analyzed by 0.8% alkaline agarose gel. The agarose gel was stained with Gelstar and analyzed as described in FIG. 14.

EXAMPLE 4

Measurement of Efficiency of RCA Reaction by [P$^{32}$] dCTP Incorporation By T7 DNA Polymerase Rolling circle amplification (RCA) reactions using T7 DNA polymerase (USB) contained 25 fmol of the pre-annealed circular template (2 pmol as nucleotides), 1 mM each of, dTTP and dGTP, and 1 mM [α-$^{32}$P] dCTP (150–300 cpm/pmol), 2.2 μg of E.coli SSB (Promega) in 25 μl reaction buffer containing 20 mM Tris-HCl (pH 7.5), 10 mM MgCl$_2$, 25 mM NaCl. Additions were performed on ice and then shifted to 37° C. Replication products were quantitated by spotting onto DE 81 filters as described by Fan, Linhua, Davey, M J, and O'Donnell, M, 1999, *Molecular Cell*, Vol.4, 541–553.

EXAMPLE 5

Measurement of Efficiency of RCA Reaction by [P$^{32}$] DCTP Incorporation by Phage φ-29 DNA Polymerase RCA reactions were carried out in 20 μl of total volume containing 50 nM circularized probes, 1 μM of rolling-circle primer, in 50 mM Tris.Hcl (pH 7.5), 10 MM MgCl$_2$, 20 mM ammonium sulfate, 1 mM each of dATP, dGTP, dTTP and 1 μCi/20 μl of ]P$^{32}$] dCTP, 5% glycerol, 4 ng/ml of yeast pyrophosphatase and Phage φ-29 DNA polymerase was added last at a concentration of 10 U/μl (approximately 100 nM). The reactions were incubated at 37° C. for 20 hours. After 20 hours the reaction was stopped by the addition of 10 mM EDTA. The reaction products were further analyzed by 0.8% alkaline agarose gel electrophoresis and the visualized by staining with Gelstar as described FIG. 17.

EXAMPLE 6

Chemical or Non-enzymatic Ligation

The chemical ligation reactions were carried out in a total volume of 100 ul in a buffer containing 50 mM MES-triethylamine (pH 6.0), 20 mM MgCl$_2$ and 10 μM of open circle (OCO) and 12 μM of bridge oligo (BO). The reaction mixture was heated at 90° C. for two minutes and allowed to cool at room temperature for 2 hours. Later the reaction mixture was left on an ice bath for 1 hour and then added freshly prepared 200 mM of water-soluble diethylaminopropyl ethyl carbodiimide hydrochloride (EDC) solution. The reaction mixture was left at 4° C. for 24 hours. After 24 hours, the reaction mixture was made up to 1.0 ml with sterile water. The samples were then desalted on a PD10 column as described above in Example 1. The sample was lyophilized overnight. After lyophilization the sample was redissolved 100 μl of in water. An aliquot (2 μl) of the reaction was analyzed in 15% TBE-Urea analytical PAGE as described in FIG. 17. The samples were further lyophilized to obtain pellets. To the pellets 10 μl of water and 20 μl of de-ionized formamide was added. Samples were heated at 90° C. for 2 minutes and then placed on an ice-water bath prior to loading onto 15% TBE-Urea polyacrylamide gel. Gels were visualized by short wave length UV shadowing at 254 nm. The lower migrating band was cut out and place in sterile siliconized 1.5 ml tube. To the gel fragment 200 μl of 3.0M sodium acetate pH 5.2 and 800 μl of water was added. Vortex thoroughly. Fix the tube horizontally to the bottom of the 37-degree orbital shaker. Set the shaker to 256 rpm and elute the circle overnight.

The following day, equilibrate a PD10 column with 40 ml of water. Centrifuge the gel fragments for a few seconds to pellet the gel chunks. Remove supernatant and place in a new siliconized tube. When PD10 column is equilibrated, load elution sample onto column and allow sample to run into column. Add water a 500 µl increments until 2.5 ml have passed through the column. Collect the next four 1.0 ml fractions in siliconized tubes. Take 50 µl aliquots from each fraction. Read absorbance at 260 nm and 280 nm using 50 µl cuvette on a UV spectrophotometer. Scan peak fractions to record spectral profile. Calculate concentration of circle product using conversion 1 OD 260-33 µg/ml. Split aliquots and store at −20 degrees. Typical yields are in the range of 40 to 42%.

The circular structure of products was confirmed by resistance to 3' exonuclease digestion reaction conditions in which a linear precircle was completely destroyed. Accordingly, the 3' exonuclease activity of T4 DNA polymerase cleaved linear precircles, but not circular products. The slightly slower gel mobility of the circles relative to the precircles was consistent with the occurrence of circularization.

EXAMPLE 7

Effect of ATP on Chemical or Non-enzymatic Ligation

The chemical ligation reactions were carried out in a total volume of 100 ul in a buffer containing 50 mM MES-triethylamine (pH 6.0), 20 mM $MgCl_2$, 10 mM ATP, 10 µm of open circle oligo and 12 µm of bridge oligo. The reaction mixture was heated at heated to 90° C. for two minutes and allowed to cool at room temperature for 2 hours. Later the reaction mixture was left on an ice bath for 1 hour and then added freshly made 200 mM diethylaminopropyl ethyl carbodiimide hydrochloride (EDC). The reaction mixture was left at 4° C. for 24 hours. After 24 hours, the reaction mixture was desalted on a PD10 column followed by lyophilization. Later, the reaction mixture was analyzed by 15% TBE-Urea analytical PAGE gel as described in FIG. 18.

EXAMPLE 8

Effect of Metal-ion on Chemical Ligation

The chemical ligation reactions were carried out in a total volume of 100 µl in a buffer containing 50 mM MES-triethylamine (pH 6.0), 20 mM $MgCl_2$, or $MnCl_2$, or $NiCl_2$, 10 µm of open circle oligo (OCO) and 12 µm of bridge oligo (BO). The reaction mixture was heated for 12 minutes at 90° C. and allowed to cool to room temperature for 2 hours. The reaction mixture was left on an ice bath for 1 hour and then added 200 mM of fresh diethylaminopropyl ethyl carbodiimide hydrochloride in water. The reaction mixture was left at 4° C. for 24 hours. After 24 hours, the reaction mixture was desalted on a PD10 column followed by lyophilisation. Later, the reaction mixture was analyzed by 15% TBE-Urea analytical PAGE gel as described in FIG. 19.

EXAMPLE 9

Effect of Metal-ion on Enzymatic Ligation

To 100 µl of 10× T-4 DNA ligase buffer pH 7.8 (USB), containing 50 mM Tris-HCl, 10 mM $MgCl_2$, 10 mM DTT, 1 mM ATP, 25 µg of bovine serum albumin in sterile tube was added 10 µm of OCO and 12.0 µm of BO. After heating to 60° C. for 30 min, the reaction mixture was allowed to cool on an ice bath for additional 30 min. To this was added 15 µl of T4 DNA ligase (USB, 200 Units/µl) and incubated at 37° C. for 2 hours (final reaction volume was 1.0 ml). An aliquot (5 µl) of reaction mixture was taken for gel analysis. Ligase reactions were stopped by heating at 90° C. for two minutes and cooling on an ice-bath prior to analysis by 15% TBE-Urea ready gel as described in FIG. 20.

EXAMPLE 10

Discrimination of Mismatch Ligation in Circle Synthesis

Figure 5:
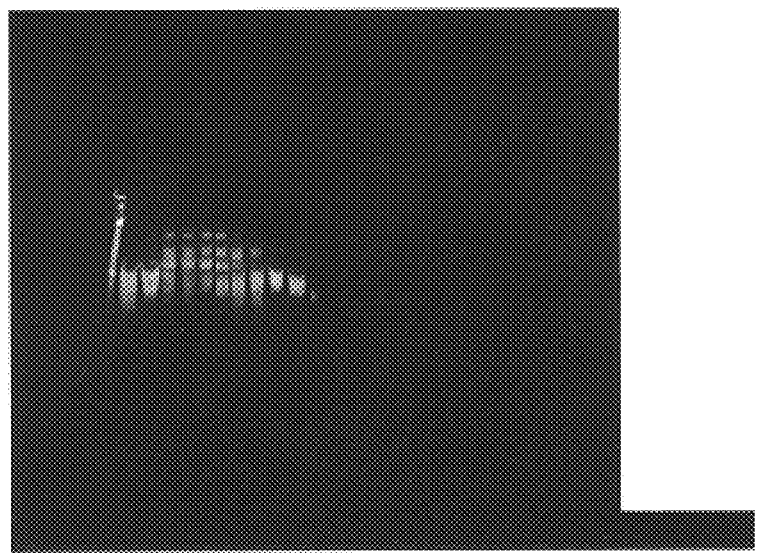
FIG. 5 shows mismatch ligation at 30 and 60 minutes using T4 DNA ligase methods. Lanes from left to right are: (1), 10 bp marker, (2) Phosphate OCP (SEQ ID NO: 12), wherein OCP=open circle probe and is to be considered synonymous with the open circle oligonucleotides (OCO) used elsewhere herein; (3) thio phosphate OCP (SEQ ID NO 13) (SEQ ID NO: 13), (4) phosphate OCP (SEQ ID NO 12) (4) and correct guide (SEQ ID NO: 14) for 30 min (5) phosphate OCP (SEQ ID NO 12) and correct guide (SEQ ID NO: 14) for 60 min (6) thio phosphate OCP and correct guide for 30 min (7) thio phosphate OCP and correct guide for 60 min (8) 5'-Phosphate OCP and mutant guide-G (SEQ ID NO: 16) for 30 min (9) 5'-Phosphate OCP and mutant guide-G (SEQ ID NO: 16) for 60 min (10) 5'-thio phosphate OCP and mutant guide G for 30 min and (11) 5'-thio phosphate OCP and mutant guide G for 60 minutes.
Figure 6:
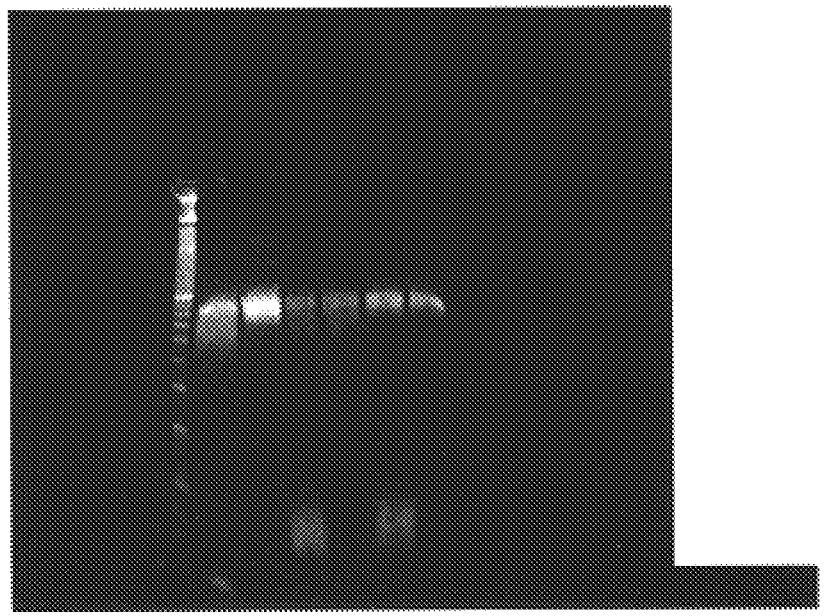
FIG. 6 shows mismatch ligation at 30 and 60 minutes using T4 DNA ligase methods. Lanes from left to right are: (1), 10 bp marker, (2)) Phosphate OCP (SEQ ID NO: 12); (3) thio phosphate OCP (SEQ ID NO 13) (SEQ ID NO: 13), (4) phosphate OCP (SEQ ID NO 12) (4) and correct guide (SEQ ID NO: 14) for 30 min (5) phosphate OCP (SEQ ID NO 12) and correct guide (SEQ ID NO: 14) for 60 min (6) thio phosphate OCP and correct guide for 30 min (7) thio phosphate OCP and correct guide for 60 min (8) 5'-Phosphate OCP and mutant guide-T (SEQ ID NO: 15) for 30 min (9) 5'-Phosphate OCP and mutant guide-T (SEQ ID NO: 16) for 60 min (10) 5'-thio phosphate OCP and mutant guide T for 30 min (11) 5'-thio phosphate OCP and mutant guide T for 60 minutes (12) Phosphate OCP and mutant guide C (SEQ ID NO: 17) for min (13) phosphate OCP and mutant C guide for 60 min and (14) thio phosphate OCP and mutant guide C for 60 min.
Figure 7:
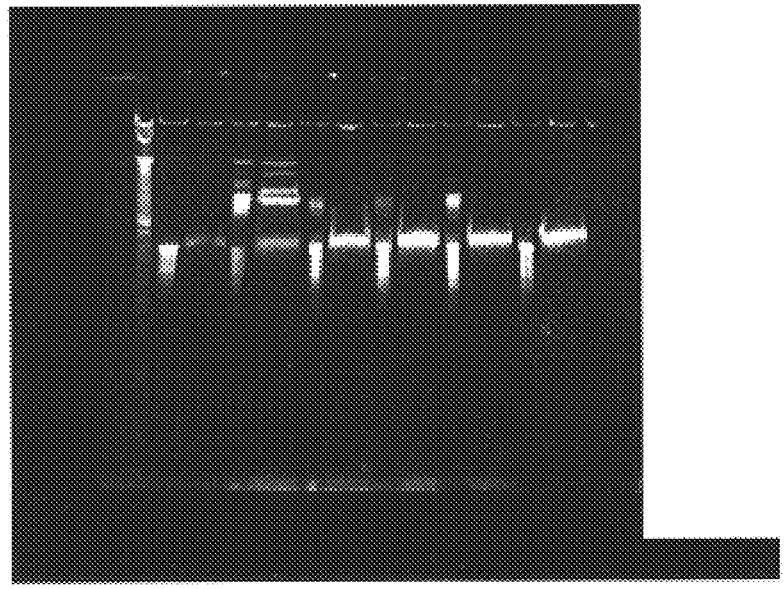
FIG. 7 shows mismatch ligation at 120 minutes using T4 DNA ligase methods. Lanes from left to right are: (1), 10 bp marker, (2) Phosphate OCP (SEQ ID NO: 12) (3) thio phosphate OCP (SEQ ID NO: 13) (4) phosphate OCP and correct guide (SEQ ID NO: 14) for 120 min (5) thiosphate OCP and correct guide (6) phosphate OCP and mutant T guide (7) thio phosphate OCP and mutant T guide (8) phosphate OCP and mutant C guide (9) thio phosphate OCP and mutant C guide (10) phosphate OCP and mutant G guide (11) thio phosphate OCP and mutant G guide (12) phosphate OCP and no guide control and (13) thio phosphate OCP and no guide control.
Figure 8:
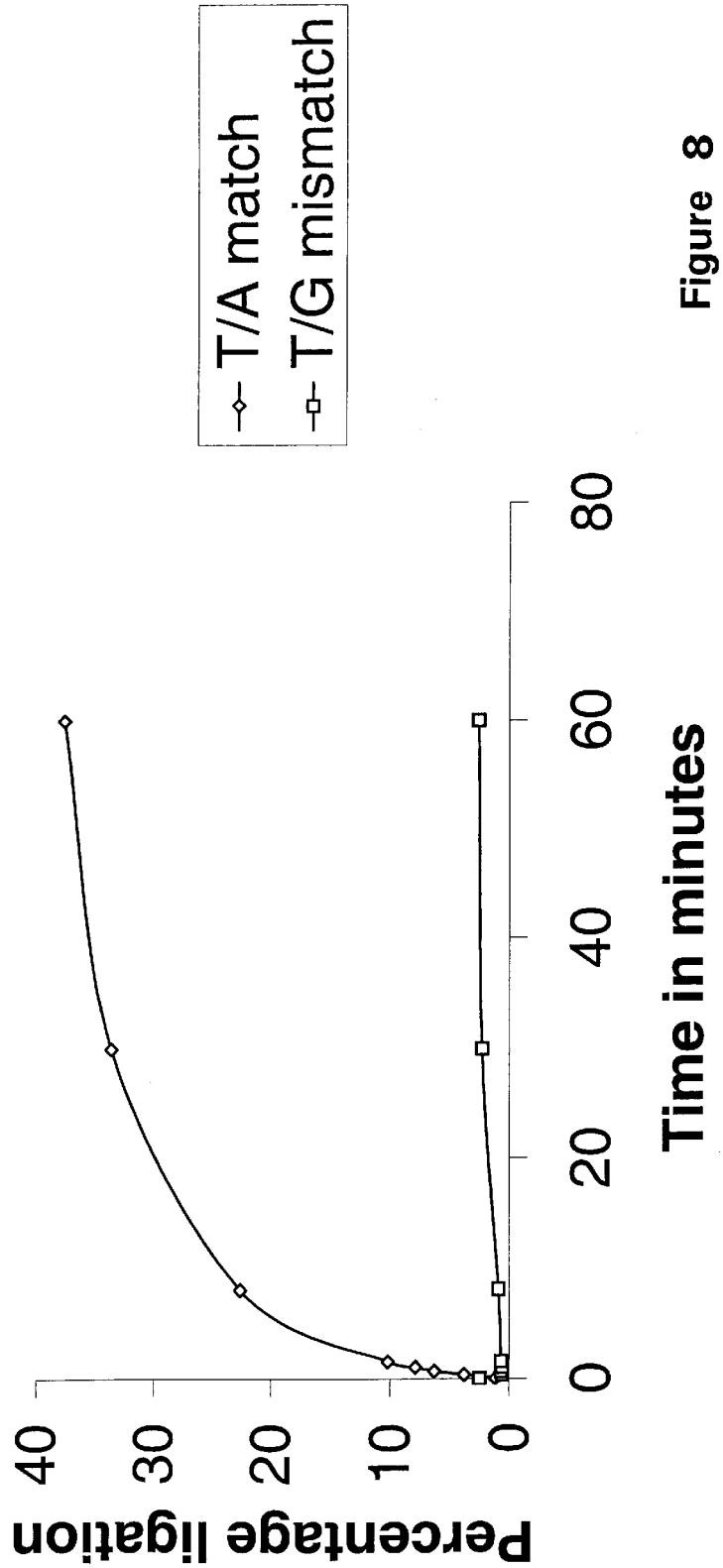
FIG. 8 shows the results of bipartite ligation with 5'-thiophosphate oligonucleotides annealed to a synthetic DNA target using Ampligase in the process of the invention. It is clear that the presence of a mismatch results in little if any circle formation.
Figure 9:
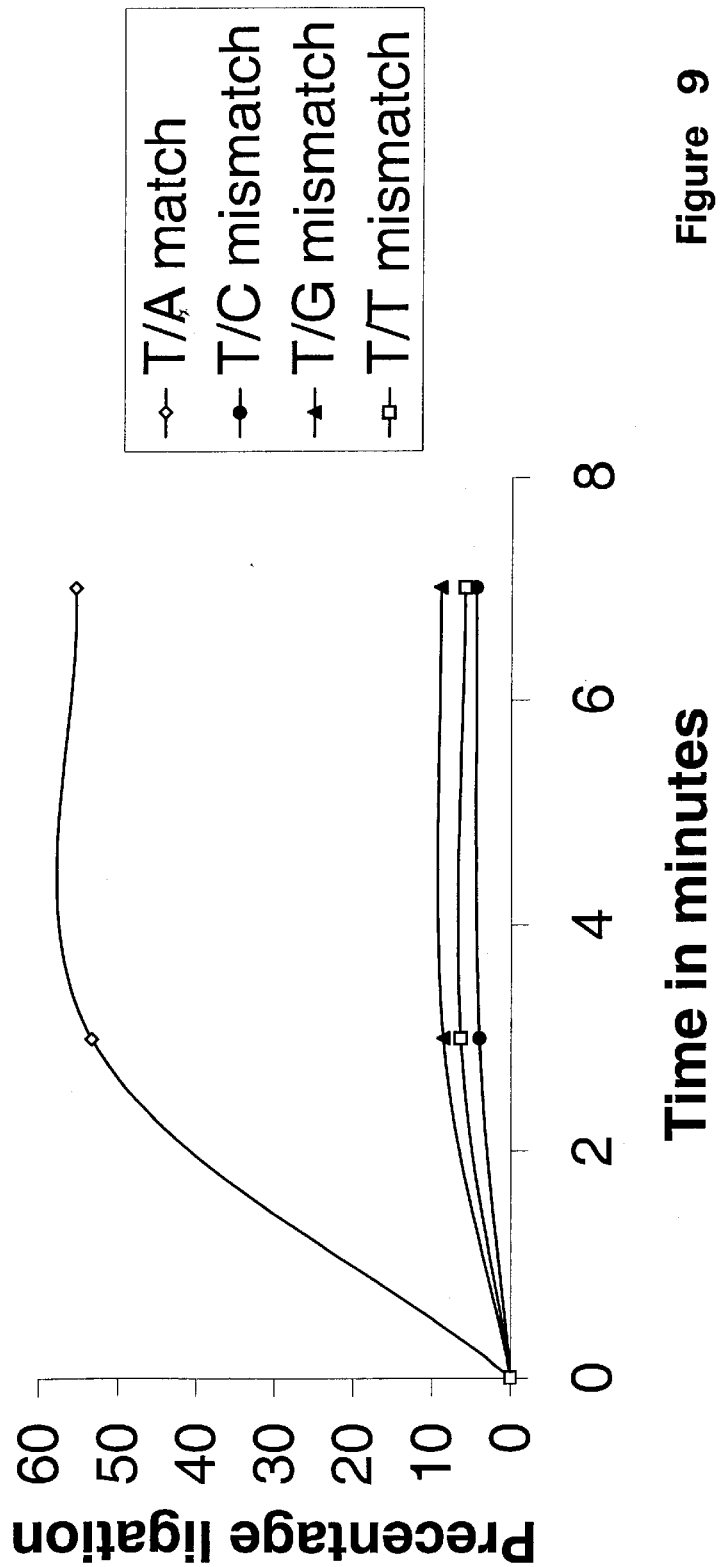
FIG. 9 shows the results of bipartite ligation with 5'-thiophosphate oligonucleotides annealed to a synthetic DNA target using T4 DNA ligase in the process of the invention. It is clear that the presence of a mismatch results in little if any circle formation.
Figure 10:
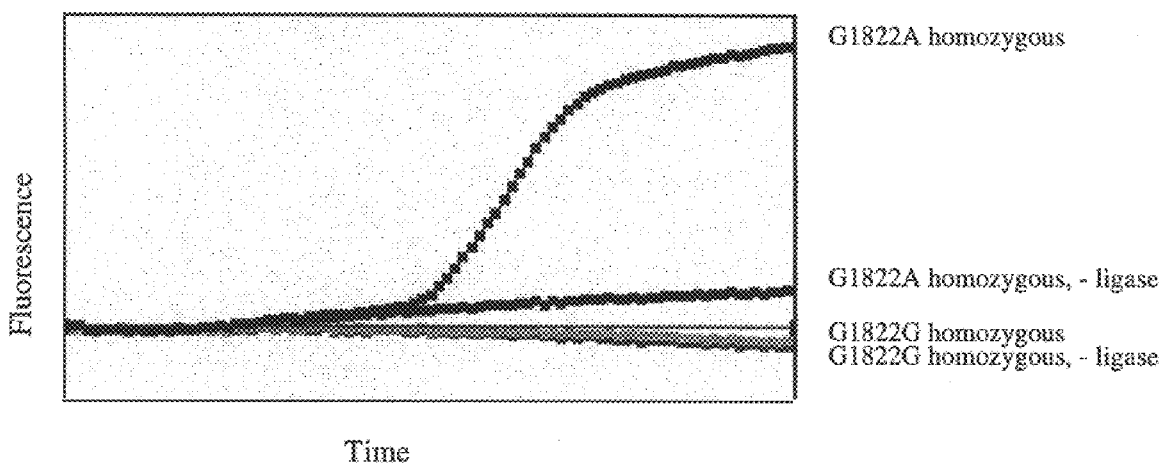
FIG. 10 shows the results of an exponential rolling circle amplification (ERCA) assay of genomic DNA containing M or GG mismatches.
Figure 11:
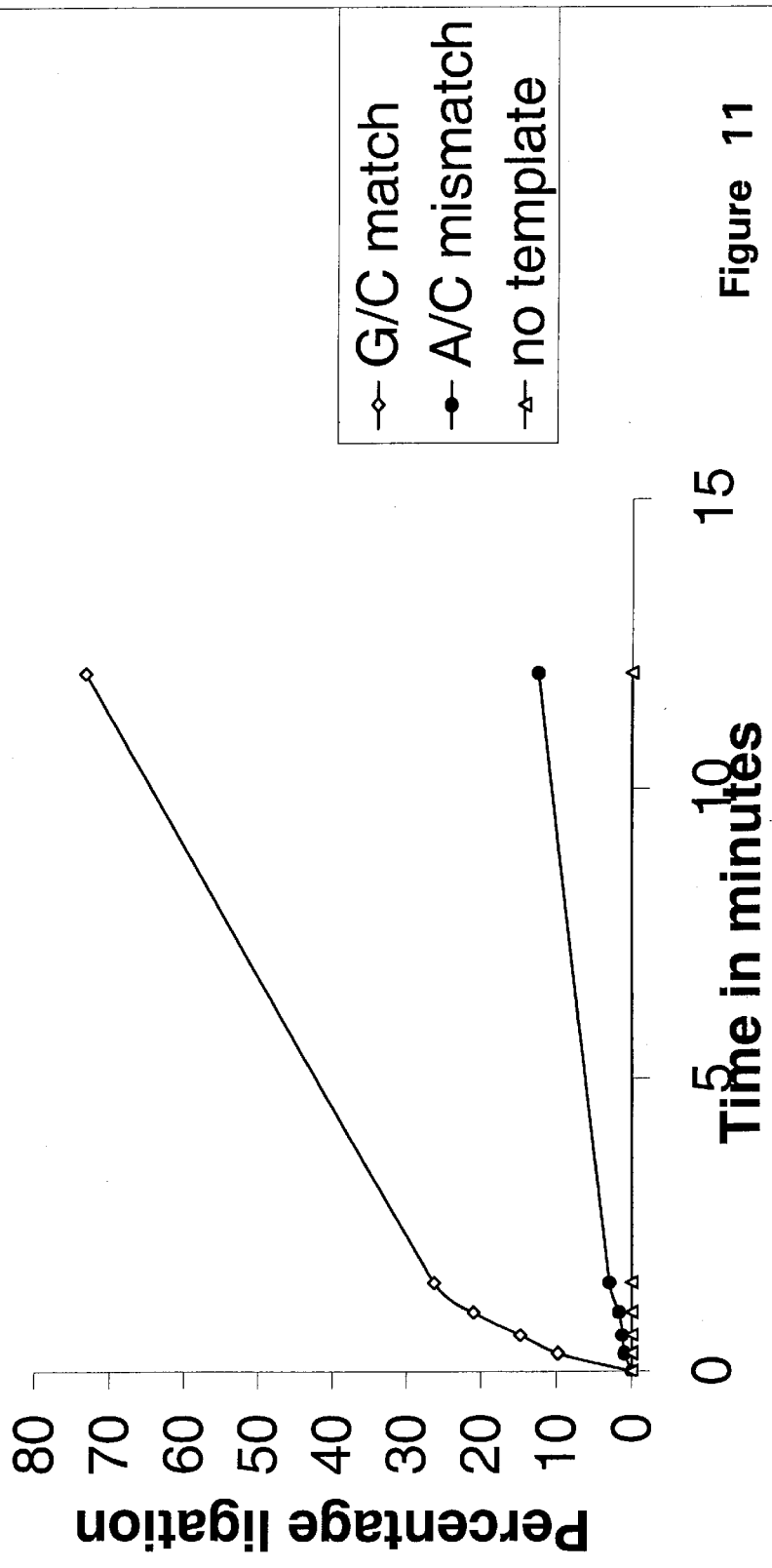
FIG. 11 shows the results of bipartite ligation with 5'-thiophosphate oligonucleotides annealed to a synthetic RNA target using T4 DNA ligase in the process of the invention. It is clear that the presence of a mismatch results in little if any circle formation.

The high efficiency of discrimination of 5'-thio phosphate directed ligation of the invention towards mismatched bases was carried out using mutant guide or target DNA with T4 DNA ligase. Here, 5 µM of linear Circle DNA thio phosphate (SEQ ID NO: 12) was ligated with 10µM of mutant target DNA sequences (SEQ ID NO: 16 or 17) under standard enzymatic ligation conditions using T4 DNA ligase. The mutations on the target DNA were placed so that the mismatch base is located exactly at the 3'-end of the linear 5'-thio phosphate of Circle 4.2 (SEQ ID NO: 12). An aliquot of sample was removed at 30 minutes, 1 hour and 2 hours after ligation and analyzed gel electrophoresis. Gel analysis of ligation reactions after staining with Gel Star staining indicate that there was no mismatch ligation product formation when 5'-thio phosphates were used as donor for ligation. However, under the identical conditions, 5'-phosphates of Circle 4.2 (SEQ ID NO: 12) has promoted T/G mismatch ligation at 30 minutes, 1 hour and 2 hours (see FIGS. 5, 6 and 7). These results demonstrate that 5'-thio phosphate ligation has very high discrimination towards mismatches like the G/T mismatch used herein. Alternatively, SNP 1822 (SEQ ID NO: 5, 6, 7 or 8) is available for use using mutant targets. Experiments can be done with either T4 DNA ligase or Ampligase.

EXAMPLE 11

Bipartite Ligation of 5'-thiophosphate Oligo Deoxy Nucleotides, Annealed to DNA Target, with T4 DNA Ligase or Ampligase Because of the resistance of thiophosphates as well as phosphorothioates to phosphatases and nucleases, these molecules will find applications in diagnostic and other uses to substitute for normal phosphate oligonucleotides. The suitability of 5' thiophosphate oligonucleotides as substrates for T4 DNA ligase, Ampligase (a thermostable DNA ligase) and T4 RNA ligase was tested using bipartite ligation between two adjacently annealed 5'thiophosphate and 3' hydroxy oligonucleotides. When annealed to target DNA or RNA oligonucleotide, 5' thiophosphate oligonucleotides undergo ligation only when ligating ends are perfectly matched with the target. The oligonucleotides with 3' mismatches with the target DNA do not participate in ligation reactions with adjacently annealed 5' thiophosphate oligonucleotides.

Here, two oligo nucleotides, 1822-3T and 5'thiophospate labeled MSI-1043 that anneal to a DNA target adjacent to each other, were used for ligation with T4 DNA ligase and Ampligase. The 5'-end of 1822-3T was labeled with $P^{32}$ phosphate to serve as a tracer for ligation experiment. These two oligonucleotides were annealed to a synthetic DNA oligonucleotide targets, 1822A or 1822C or 1822G or 1822T, with either matched or mismatched nucleotides at the 3'-end of 1822-3T. These annealed (or hybridized) oligo duplexes were treated with either T4 DNA ligase or Ampligase for indicated intervals of time and ligated reaction mixture was analyzed by polyacrylamide gel electrophoresis (PAGE) and auto-radiography. Quantitation of unligated product (29 nt long) and ligated product (59 nt long) showed the efficiency of detection by the ligation method of the invention.

EXAMPLE 12

SNP Genotyping with 5' Thiphosphate Open Circle Probes: Genotyping of 1822 GG and 1822AA Genomic DNA with Thiophosphate OCP.

In current methods for detecting single nucleotide polymorphisms (SNPs), for each SNP, two linear, allele-specific probes are designed that circularize when they anneal to the target sequence. Each probe consists of a single oligonucleotide, 80–90 bases in length. The 5'-end of the probe is phosphorylated and bears a sequence of 20 nucleotides that will hybridize to the region immediately 5'-of the SNP. The 3'-end of the probe contains 10–20 nucleotides complementary to the region immediately 3'- of the SNP. Both allele-specific probes are identical with the exception of the 3'-base, which is varied to complement the polymorphism site. It is this base that confers the ability of the probe to fully and specifically hybridize to only one allele and makes multiplexing of two alleles per well possible. Sandwiched between the allele-specific probe arms is a backbone sequence of 40–50 nucleotides that encodes binding sites for two RCA amplification primers. The two backbone sequences are generic to every SNP oligonucleotide pair but different between the two oligonucleotides. Optimizing the design of these primers in this way reduces costs by ensuring the same backbone-directed primers can be used in subsequent RCA reactions.

The major disadvantage in so-called padlock-based assays is that for every SNP two new padlocks are required. In addition, mismatch ligation is often a major serious problem. Currently mismatch ligation in such assays is minimized by reducing reaction time, shortening the arms of padlock and/or incorporating mismatches at either 3' or 5'-arms close to ligation site. However, these methods do not stop mismatch ligation. To circumvent mismatch ligation in such an assay, 5'-thiophosphates of linear padlock DNA of SNP 1822 were designed. Both Ampligase and T-4 DNA ligase can be used in such assays.

The G1822A or G1822G SNP on human chromosome 13q32 was used for genotyping with 5' thiophosphate OCPs (open circular probes) using the SNP assay. Human genomic DNA carrying either homozygous AA or GG alleles was digested with the restriction endonuclease Alu I and assayed in two different tubes. Each tube contained 0.125 pM G1822A-specific OCP and 100 ng of either G1822A or G1822G genomic DNA corresponding to a gene copy number of approximately 30,000. OCP ligation was performed with Ampligase for 30 min at 60° C., approximately 15° C. above the Tm for the OCP 3' arm, in order to maximize specificity of ligation. Since the 5' arm of the OCP has a Tm (melting temperature) above that of the ligation temperature, the 5' arm hybridizes to its target in a stable manner, and SNP specificity is achieved via the 3'-arm.

The isothermal ERCA reactions were performed at 60° C. using Bst DNA polymerase. The reactions contained 1 uM each of appropriate OCP-specific P1 Amplifluor primer (P1ocTET) and the corresponding allele-specific P2 (P2ocT) and OCP ligation mixture with either G1822A or G1822G homozygous genomic DNA. When the T at the 3' end of the OCP was matching with the A allele at the genomic DNA, a fluorescent signal was detected. Only background fluorescence was detected when either G1822G homozygous DNA was used or Ampligase was omitted from the reaction medium for the mismatched OCPs.

EXAMPLE 13

Bipartite Ligation of Oligo Deoxy-nucleotides, Annealed to RNA Target, with T4 RNA Ligase:

The enzymatic phosphorothioate ligation approach as described above is mainly carried out on DNA/DNA duplexes formed between DNA probe and the target DNA. However, viruses such as HIV, HBV, HCV and HPV that cause several of the diseases predominantly do carry RNA as their principal target. Ligation of DNA on a RNA target is a very challenging problem. Many of the DNA ligases do not work very well on RNA targets. To circumvent this problem, an RNA ligase based procedure was developed. In addition, ligation of DNA probe on a RNA target is known to be non-discriminatory due to the stable secondary structure present in many RNA target.

In order to test the applicability of 5'-thiophosphate oligodeoxy nucleotides as substrates for T4 RNA ligase, M3 RNA target oligoribonucleotide was annealed to either $P^{32}$ labeled M3'GL and MSI-1074 with 5' thiophosphate or P32 labelled M3'TL and MSI-1074. The annealed duplex was treated with T4RNA ligase for indicated intervals of time. The ligation products were identified on denaturing 12% PAGE. The percentage of ligation was calculated by quantitating the relative amounts of $P^{32}$ labeled unligated oligo (22 nt long) and ligated oligo (42 nt long) by autoradiography on phosphoimager equipment.

Genomic DNA samples were digested with the restriction endonuclease Alu I before being used as template in the ligation reaction. Amplifluor® is a trademark of Intergen Company. Ampligase® is a trademark of Epicentre Technologies Corp.

EXAMPLE 14

SNP Assay with 5'-thiophosphate OCP: DNA Annealing and Ligation Followed by ERCA Reaction The reactions were set up in 96-well MicroAmp Optical plates (Perkin Elmer) in a 10 µl reaction volume containing 1 U Ampligase (Epicentre Technologies), 20 mM Tris-HCl (pH 8.3), 25 mM KCl, 10 mM $MgCl_2$, 0.5 mM NAD, and 0.01% Triton® X-100. Standard reactions contained 0.125–0.5 pM OCP and 100 ng of Alu I digested genomic DNA. DNA was denatured by heating the reactions at 95° C. for 3 min followed by annealing and ligation at 60° C. for 20 min. 20 µl of ERCA mix was added to 10 µl ligation reaction. The ERCA mix contained 5% tetramethyl ammonium oxalate, 400 µM dNTP mix, 1 uM each of the two primers, 8 u of Bst polymerase (New England Biolabs, Mass.), and 1×modified ThermoPol reaction buffer containing 20 mM Tris-HCl (pH 8.8), 10 mM KCl, 10 mM $(NH_4)_2SO_4$ and 0.1% Triton X-100. ERCA reactions were performed in the Real-Time ABI 7700 Sequence Detector (Perkin Elmer).

TABLE 1

Sequence Used in the Experiments.

M3, RNA target
All ribo-5'-GAG UGU CGU CGG AAA UUG GCA GUA UUU CUU UCC UGU GAU-3' (SEQ ID NO:1)

M3'GL
5'-ATT ACG GTG AAA AGA AAT ACT G-3' (SEQ ID NO:2)

M3'AL
5'-ATT ACG GTG AAA AGA AAT ACT A-3' (SEQ ID NO:3)

MSI-1074
5'thiophosphate-CCA ATT TCC GAC GTT TCT GA-3' (SEQ ID NO:4)

1822A target
5'-AAA AGT AGT AAA TCT GTC CAG TTC TTC AAC AAA GCA GAA CAT CTG CAA ACT AAA A-3' (SEQ ID NO:5)

1822C target
5'-AAA AGT AGT AAA TCT GTC CAG TTC TTC CAC AAA GCA GAA CAT CTG CAA ACT AAA A-3' (SEQ ID NO:6)

1822G target
5'-AAA AGT AGT AAA TCT GTC CAG TTC TTC GAC AAA GCA GAA CAT CTG CAA ACT AAA A-3' (SEQ ID NO:7)

1822T target
5'-AAA AGT AGT AAA TCT GTC CAG TTC TTC TAC AAA GCA GAA CAT CTG CAA ACT AAA A-3' (SEQ ID NO:8)

MSI-1043
5'-thiophosphate-GAA GAA CTG GAG AGA TTT ACT ACG TGA CTC-3' (SEQ ID NO:9)

1822-3T
5'-TAC TCC CTC TTG AGA TGT TCT GCT TTG TT-3' (SEQ ID NO:10)

MSI-997 (1822-T, thiophosphate OCP)
5'-thiophosphate-GAA GAA CTG GAC AGA TTT ACT ACG TAT GTT GAC TGG TCA CAC GTC GTT CTA GTA CGC TTC TAC TCC CTC TTG AGA TGT TCT GCT TTG TT-3' (SEQ ID NO:11)

MSI-789
5'-Phosphate-ACTGACGAGCTACTGAGACATGTACAATCGGACCTGTGAGGTACTACCCTA ATCGGACCTGTGAGGTACTACCCTAACTT-3' (SEQ ID NO:12)

MIS-894
5'-Phosphorothioate-ACTGACGAGCTACTGAGACATGTACAATCG GACCTGTGAGGTACTACCCTAATCGGACCTGT GAGGTACTACCCTAACTT-3' (SEQ ID NO:13)

PA-83: Correct circle 4.2 guide sequence: 5'-TCG TCA GT A AGT TAG-3' (SEQ ID NO:14)

Mutant T circle 4.2 guide sequence: 5'-TCG TCA GT T AGT TAG-3' (SEQ ID NO:15)

Mutant G cirlce 4.2 guide sequence: 5'-TCG TCA GT G AGT TAG-3' (SEQ ID NO:16)

Mutant C guide sequence: 5'-TCG TCA GT C AGT TAG-3' (SEQ ID NO:17)

5'-Phosphate-CTC AGC TGT GTA ACA ACA TGA AGA TTG TAG GTC AGA ACT CAC CTG TTA GAA ACT GTG AAG ATC GCT TAT TAT GTC CTA TC-3' (SEQ ID NO:18)

5'-Phosphorothioate-CTC AGC TGT GTA ACA ACA TGA AGA TTG TAG GTC AGA ACT CAC CTG TTA GAA ACT GTG AAG ATC GCT TAT TAT GTC CTA TC-3' (SEQ ID NO:19)

5'-Phosphate-TAG CAC GGA CAT ATA TGA TGG TAC CGC AGT ATG AGT ATC TCC TAT CAC TAC TAA GTG GAA GAA ATG TAA CTG TTT CTT TC-3' (SEQ ID NO:20)

5'-Phosphate-TAG CAC GGA CAT ATA TGA TGG TAC CGC AGT ATG AGT ATC TCC TAT CAC TAC TAA GTG GAA GAA ATG TAA CTG TTT CCT TC-3' (SEQ ID NO:21)

5'-CAC AGC TGA GGA TAG GAC AT-3' (SEQ ID NO:22)

5'-AGT CCG TGC TAG AAG AAA CAG TAC A-3' (SEQ ID NO:23)

Phosphate Circle
CTC AGC TGT GTA ACA ACA TGA AGA TTG TAG GTC AGA ACT CAC CTG TTA GAA ACT GTG AAG ATC GCT TAT TAT GTC CTA TC (SEQ ID NO:24)

TABLE 1-continued

Sequence Used in the Experiments.

Phosphorothioate Circle
CTC AGC TGT GTA ACA ACA TGA AGA TTG TAG GTC AGA ACT CAC CTG     (SEQ ID NO:25)
TTA GAA ACT GTG AAG ATC GCT TAT TAT GTC CTA TC Phosphate Circle 80 bases
TAG CAC GGA CAT ATA TGA TGG TAC CGC AGT ATG AGT ATC TCC TAT     (SEQ ID NO:26)
CAC TAC TAA GTG GAA GAA ATG TAA CTG TTT CCT TC Phosphorothioate circle 80 bases
TAG CAC GGA CAT ATA TGA TGG TAC CGC AGT ATG AGT ATC TCC TAT     (SEQ ID NO:27)
CAC TAC TAA GTG GAA GAA ATG TAA CTG TTT CCT TC

5'-CAC AGC TGA GGA TAG GAC AT-3'                                (SEQ ID NO:28)

5'-ACGTCGTCCGTGCTAGAAGGAAACACGCA-3'                             (SEQ ID NO:29)

References

1. Doherty, A. J. and Suh, S. W. (2000) *Nucleic Acids Res,* 28, No.21, 4051–4058.
2. Engler, M. J. Richardson, C. C. (1982) In Boyer, P. D. (ed), *The Enzymes,* Academic Press, New York, Vol. XV, pp. 3–29.
3. Lindahl, T. and Barnes, D. E. (1992) *Annu. Rev. Biochem.* 61, 251–281.
4. Lehman, I. R. (1974) *Science,* 186, 790–797.
5. Higgins, N. P. and Cozzarelli, N. R. (1979) *Methods Enzymol.* 68, 50–71.
6. Sgaramella, V. and Khorana, H. G. (1972) *J. Mol. Biol.,* 72, 493–502.
7. Deugau, K. V. and Van de Sande, J. H. (1978) *Biochemistry,* 17, 723–729.
8. Alves, A. M. and Carr, F. J. (1988) *Nucleic Acids Res.,* 16, 8723.
9. Wu, D. Y. and Wallace, R. B. (1989) *Gene,* 76, 245–254.
10. Landegren, U., Kaiser, R., Sanders, J. and Hood, L. (1989) *Science,* 241, 1077–1080.
11. Wu, D. Y. and Wallace, R. B. (1989) *Genomics,* 4, 560–569.
12. Takahashi, M., Yamaguchi, E. and Uchida, T. (1984) *J. Biol. Chem.,* 259, 10041–10047.
13. Luo, J., Bergstrom, D. E. and Barany, F. (1996) *Nucleic Acids Res.,* 24, 3071–3078.
14. Barany, F. (1991) *Proc. Natl Acad. Sci. USA,* 88, 189–193.
15. Wiedmann, M, Wilson, W. J., Czajka, J., Luo, J., Barany, F. and Batt, C. A. (1994) *PCR Methods Appl.,* 4, 551–564.
16. Lehman, T. A., Scott, F., Seddon, M., Kelly, K., Dempsey, E. C., Wilson, V. L., Mulshine, J. L. and Modali, R. (1996) *Anal. Biochem.* 239, 153–159.
17. Gryaznov, S. M. and Letsinger, R. L. (1993) *J. Am. Chem. Soc.,* 115, 3808–3809.
18. Gryaznov, S. M. and Letsinger, R. L. (1993) *Nucleic Acids Res.,* 21, 1403–1408.
19. Gryaznov, S. M., Schultz, R., Chaturved, S. K. and Letsinger, R. L (1994) *Nucleic Acids Res.,* 22, 2366–2369.
20. Luo, P., Leitzel, J. C., Zhan, Z. and Lynn, D. G. (1998) *J. Am. Chem. Soc.,* 120, 3019–3031.
21. Li, T., Weinstein, D. S. and Nicolaou, K. C. (1997) *Chem. Biol.,* 4, 209–214
22. Wang, S. and Kool, E. T. (1994) *Nucleic Acids Res.,* 22, 2326–2333.
23. Ferentz, A. E. and Verdine, G. L. (1991) *J. Am. Chem. Soc.,* 113, 4000–4002.
24. Kanaya, E. and Yanagawa, H. (1986) *Biochemistry,* 25, 7423–7430.
25. Ashley, G. W. and Kushlan, D. M. (1991) *Biochemistry,* 30, 2927–2933Sokolova, N. I., Ashirbekova, D. T., Dolinnaya, N. G. and Shabarova, Z. A. (1988) *FEBS Lett.* 232, 153–155.
26. Sievers, D. and von Kiedrowski, G. (1994) *Nature,* 369, 221–224Letsinger, R. L., Wu, T. and Elghanian, R. (1997) *Nucleosides Nucleotides,* 16, 643–652.
27. Liu, J. and Taylor, J.-S. (1998) *Nucleic Acids Res.,* 26, 3300–3304Xu, Y, and Kool, E. T., (1998), *Nucleic Acids, Res.,* 26 (130, 3159–3164, and references cited therein.
28. Olsen, D. B., Kotzorek, G., Sayers, J. R. and Eckstein, F. (1990) *J. Biol. Chem.,* 265, 14389–14394. Van Tol, H., Buzayan, J. M., Feldstein, P. A., Eckstein, F. and Bruening, G. (1990) *Nucleic Acids Res.,* 18, 1971–1975Slim, G. and Gait, M. J. (1991) *Nucleic Acids Res.,* 19, 1183–1188. Suh, E. and Waring, R. B. (1992) *Nucleic Acids Res.,* 20, 6303–6309. Heidenreich, O., Pieken, W. and Eckstein, F. (1993) *FASEB J.,* 7, 90–96. Eckstein, F. and Thomson, J. B. (1995) *Methods Enzymol.* 262, 189–202. Reese, C. B., Simons, C. and Pei-Zhuo, Z. (1994) *J. Chem. Soc. Chem. Commun.* 1809–1810.
29. Johnson, R., Reese, C. B. and Pei-Zhuo, Z. (1995) *Tetrahedron,* 54, 5093–5098.
30. Dantzman, C. L. and Kiessling, L. L. (1996) *J. Am. Chem. Soc.,* 118, 11715–11719.
31. Michelson, A. M. (1962) *J. Chem. Soc.,* 979–982.
32. Liu, X. and Reese, C. B. (1995) *Tetrahedron Lett.* 36, 3413–3416.
33. Kuimelis, R. G. and McLaughlin, L. W. (1995) *Nucleic Acids Res.,* 23, 4753–4760.
34. Weinstein, L. B., Earnshaw, D. I., Cosstick, R. and Cech, T. R. (1996) *J. Am. Chem. Soc.,* 118, 10341–10350.
35. Kuimelis, R. G. and McLaughlin, L. W. (1996) *Biochemistry,* 35, 5308–5317. Liu, X. and Reese, C. B. (1996) *Tetrahedron Lett.* 37, 925–928.
36. Cook, A. F. (1970) *J. Am. Chem. Soc.,* 92, 190–195.
37. Chladek, S. and Nagyvary, J. (1972) *J. Am. Chem. Soc.,* 94, 2079–2084.
38. Rybakov, V. N., Rivkin, M. I. and Kumarev, V. P. (1981) *Nucleic Acids Res.,* 9, 189–201.
39. Cosstick, R. and Vyle, J. S. (1988) *J. Chem. Soc. Chem. Commun.* 992–993.
40. Cosstick, R. and Vyle, J. S. (1989) *Tetrahedron Lett.* 30, 4693–4696.
41. Cosstick, R. and Vyle, J. S. (1990) *Nucleic Acids Res.,* 18, 829–835.
42. Mag, M., Luking, S. and Engels, J. W. (1991) *Nucleic Acids Res.,* 19, 1437–1441.
43. Li, X., Andrews, D. M. and Cosstick, R. (1992) *Tetrahedron,* 48, 2729–2738.

44. Vyle, J. S., Li, X. and Cosstick, R. (1992) *Tetrahedron Lett.* 33, 3017–3020.
45. Vyle, J. S., Connolly, B., Kemp, D. and Cosstick, R. (1992) *Biochemistry,* 31, 3012–3018.
46. Matzura, H, and Eckstein, F. (1968), Eur. J. Biochem. 3, 448–452.
47. Eckstein, F, and Gindl, H. (1970), Eur. J. Biochem. 13, 558–564.
48. Eckstein, F. et. al. (1976), Proc. Natl. Acad. Sci. USA. 73, 2987–2990.
49. Burgers, P. M. J, and Eckstein, F. (1978), Proc. Natl. Acad. Sci. USA. 75, 4798–4800.
50. Brady, R. S. et. al., (1982), Biochemistry, 21, 2570–2572.
51. Eckstein, F, and Jovin, T. M. (1983), Biochemistry, 22, 4546–4550.
52. Bartlett, P. A, and Eckstein, F. (1982), J. Biol. Chem, 257, 8879–8884.
53. Burgers, P. M. J, and Eckstein, F. (1979), Biochemistry, 18, 450–454.
54. Marlier, J. F. et. al., (1981), Biochemistry, 20, 2212–2219.
55. Eckstein, F. et. al., (1977), Biochemistry, 16, 3429–3432.
56. Bryant, F. R, and Benkovic, F. J, (1982), Biochemistry, 21, 5877–5885
57. Suhadolink, R. J, and Choongeun, L. (1985), Biochemistry, 24, 551–555.
58. Matzura, H, and Eckstein, F. (1968) Eur. J. Biochem, 3, 448–452.
59. Eckstein, F, and Gindi, H. (1970). Eur. J. Biochem. 13, 558–564.
60. Eckstein, F. et. al. (1976), Proc. Natl. Acad. Sci. USA, 73,m 2987–2990.
61. Burgers, P. M. J, and Eckstein, F. (1978), Proc. Natl. Acad. Sci. USA, 75, 4798–4800.
62. Brady, R. S. et. al. (1982), Biochemistry, 21, 2570–2572.
63. Eckstein, F, and Jovin, T. M. (1983), Biochemistry, 22, 4546–4550.
64. Bartlett, P. A, and Eckstein, F. (1982), J. Biol. Chem, 257, 8879–8884.
65. Burgers, P. M. J, and Eckstein, F. (1979), Biochemistry, 18, 450–454.
66. Marlier, J. F, et. al., (1981), Biochemistry, 20, 2212–2219.
67. Eckstein, F., et. al., (1977), Biochemistry, 16, 3429–3432.
68. Bryant, F. R, and Benkovic, S. J. (1982), Biochemistry, 5877–5885.
69. Suhadolink, R. J, and Chooneun, L. (1985), Biochemistry, 24, 551–555.
70. Kariko, K. et. al., (1987), Biochemistry, 26, 7127–7135.
71. Lizardi, P. M, Huang, Xiaohua, Zhengrong, Zhu, Bray-Ward, P, Thomas, D. C., and Ward, D. C., (1998), Nature Genetics, 19, 225–232.
72. Fire, A and Xu, S. Q, (1995), Proc. Natl. Acad. Sci. USA 92, 4641–4645; Liu, D, Daubendiek, S. L., Ziliman, M. A., Ryan, K, and Kool, E. T., (1996), J. Am. Chem. Soc., 118, 1587–1594.

What is claimed is:

1. A process for forming a single stranded circular oligonucleotide comprising contacting 3'-hydroxyl and 5'-phosphorothioate groups of an open circle oligonucleotide (OCO), having such groups at its 3'- and 5'-ends, with a bridging oligonucleotide (BO), said BO comprising sequences complementary to sequences at the 3'- and 5'-ends of said OCO, in the presence of a ligation catalyst that directs formation of a 3'-5'-phosphodiester linkage with the sulfur atom of said 5'-phosphorothioate group not present as a bridging atom thereby forming a single-stranded circular oligonucleotide.

2. The process of claim 1 wherein said catalyst is N-ethyl-N'-(dimethylaminopropyl)-carbodiimide hydrochloride (EDC).

3. The process of claim 1 wherein said catalyst is an enzyme.

4. The process of claim 3 wherein said enzyme is a ligase.

5. The process of claim 4 wherein said ligase is a ligase that forms a phosphodiester linkage at a nick in duplex DNA containing phosphorothioate at the 5'-end of said nick.

6. The process of claim 5 wherein said ligase is selected from the group consisting of T4 DNA ligase, *E. coli* DNA ligase, Taq DNA ligase, Tth DNA ligase, *Thermus scotoductus* DNA ligase, *Rhodothermus marinus* DNA ligase, Ampligase, Bst ligase, T4 RNA ligase and cappases.

7. The process of claim 6 wherein said ligase is present along with ATP and NAD.

8. The process of claim 7 wherein said ligase is T4 DNA ligase and Ampligase.

9. The process of claim 1 further comprising the step of removing said bridging oligonucleotide from said single-stranded circular oligonucleotide.

10. The process of claim 1 wherein said OCO and said BO are annealed prior to contacting said 3'-OH and 5'-phosphorothioate groups.

11. The process of claim 1 wherein said BO and said OCO are present in the mole ratio of about 1 to 1, respectively.

12. The process of claim 1 wherein the molar concentration of BO is greater than that of OCO.

13. The process of claim 1 wherein said OCO and said BO are deoxyribonucleotides.

14. The process of claim 1 wherein said OCO is a DNA and said BO is RNA.

15. The single-stranded circular oligonucleotide formed by the process of claim 1.

16. The single-stranded circular oligonucleotide of claim 15 wherein said single-stranded circular oligonucleotide is conjugated with peptides, proteins, detection labels and primer sequences.

17. A process for amplifying a selected oligonucleotide sequence comprising rolling circle amplification (RCA) using an amplification target circle (ATC) formed by the process of claim 1.

18. A process for amplifying a selected oligonucleotide sequence comprising rolling circle amplification (RCA) using an amplification target circle (ATC) formed by the process of claim 1.

19. The process of claim 1 wherein said bridging oligonucleotide complementary sequences include a nucleotide complementary to either the 3'-nucleotide of said OCO or the 5'-nucleotide of said OCO.

20. The process of claim 1 wherein said bridging oligonucleotide complementary sequences include a nucleotide complementary to the 3'-OH nucleotide of said OCO and a nucleotide complementary to the 5'-nucleotide of the OCO.

21. The single-stranded circular oligonucleotide formed by the process of claim 9.

22. The single-stranded circular oligonucleotide of claim 21 wherein said single-stranded circular oligonucleotide is conjugated with peptides, proteins, detection labels and primer sequences.

* * * * *

SEQUENCE LISTING

<160> NUMBER OF SEQ ID NOS: 29

<210> SEQ ID NO 1
<211> LENGTH: 39
<212> TYPE: RNA
<213> ORGANISM: Artificial Sequence
<220> FEATURE:
<223> OTHER INFORMATION: RNA target oligonucleotide.

<400> SEQUENCE: 1
gagugucguc ggaaauuggc aguauuucuu uccgugau          39

<210> SEQ ID NO 2
<211> LENGTH: 22
<212> TYPE: DNA
<213> ORGANISM: Artificial Sequence
<220> FEATURE:
<223> OTHER INFORMATION: Oligonucleotide sequence.

<400> SEQUENCE: 2
attacggtgg aaagaaatac tg          22

<210> SEQ ID NO 3
<211> LENGTH: 22
<212> TYPE: DNA
<213> ORGANISM: Artificial Sequence
<220> FEATURE:
<223> OTHER INFORMATION: Oligonucleotide sequence.

<400> SEQUENCE: 3
attacggtgg aaagaaatac ta          22

<210> SEQ ID NO 4

```
<211> LENGTH: 20
<212> TYPE: DNA
<213> ORGANISM: Artificial Sequence
<220> FEATURE:
<223> OTHER INFORMATION: 5'-Thiophosphate oligonucleotide.

<400> SEQUENCE: 4
ccaatttccg acgtttctga                                              20

<210> SEQ ID NO 5
<211> LENGTH: 55
<212> TYPE: DNA
<213> ORGANISM: Artificial Sequence
<220> FEATURE:
<223> OTHER INFORMATION: Target oligonucleotide with mismatched base.

<400> SEQUENCE: 5
aaaagtagta aatctgtcca gttcttcaac aaagcagaac atctgcaaac taaaa       55

<210> SEQ ID NO 6
<211> LENGTH: 55
<212> TYPE: DNA
<213> ORGANISM: Artificial Sequence
<220> FEATURE:
<223> OTHER INFORMATION: Target oligonucleotide with mismatched base.

<400> SEQUENCE: 6
aaaagtagta aatctgtcca gttcttccac aaagcagaac atctgcaaac taaaa       55

<210> SEQ ID NO 7
<211> LENGTH: 55
<212> TYPE: DNA
<213> ORGANISM: Artificial Sequence
<220> FEATURE:
<223> OTHER INFORMATION: Target oligonucleotide with mismatched base.

<400> SEQUENCE: 7
aaaagtagta aatctgtcca gttcttcgac aaagcagaac atctgcaaac taaaa       55

<210> SEQ ID NO 8
<211> LENGTH: 55
<212> TYPE: DNA
<213> ORGANISM: Artificial Sequence
<220> FEATURE:
<223> OTHER INFORMATION: Target oligonucleotide with mismatched base.

<400> SEQUENCE: 8
aaaagtagta aatctgtcca gttcttctac aaagcagaac atctgcaaac taaaa       55

<210> SEQ ID NO 9
<211> LENGTH: 30
<212> TYPE: DNA
<213> ORGANISM: Artificial Sequence
<220> FEATURE:
<223> OTHER INFORMATION: 5'-Thiophosphate oligonucleotide.

<400> SEQUENCE: 9
gaagaactgg acagatttac tacgtgactc                                   30

<210> SEQ ID NO 10
<211> LENGTH: 29
<212> TYPE: DNA
<213> ORGANISM: Artificial Sequence
<220> FEATURE:
<223> OTHER INFORMATION: Oligonucleotide for ligation.

<400> SEQUENCE: 10
```

```
tactccctct tgagatgttc tgctttgtt                                        29

<210> SEQ ID NO 11
<211> LENGTH: 89
<212> TYPE: DNA
<213> ORGANISM: Artificial Sequence
<220> FEATURE:
<223> OTHER INFORMATION: 5'-Thiophosphate oligonucleotide.

<400> SEQUENCE: 11
gaagaactgg acagatttac tacgtatgtt gactggtcac acgtcgttct agtacgcttc      60
tactccctct tgagatgttc tgctttgtt                                        89

<210> SEQ ID NO 12
<211> LENGTH: 80
<212> TYPE: DNA
<213> ORGANISM: Artificial Sequence
<220> FEATURE:
<223> OTHER INFORMATION: 5'-Phosphate Oligonucleotide.

<400> SEQUENCE: 12
actgacgagc tactgagaca tgtacaatcg gacctgtgag gtactaccct aatcggacct      60
gtgaggtact accctaactt                                                  80

<210> SEQ ID NO 13
<211> LENGTH: 80
<212> TYPE: DNA
<213> ORGANISM: Artificial Sequence
<220> FEATURE:
<223> OTHER INFORMATION: 5'-Phosphorothioate oligonucleotide for
      ligation.

<400> SEQUENCE: 13
actgacgagc tactgagaca tgtacaatcg gacctgtgag gtactaccct aatcggacct      60
gtgaggtact accctaactt                                                  80

<210> SEQ ID NO 14
<211> LENGTH: 15
<212> TYPE: DNA
<213> ORGANISM: Artificial Sequence
<220> FEATURE:
<223> OTHER INFORMATION: Circular Guide Sequence oligonucleotide.

<400> SEQUENCE: 14
tcgtcagtaa gttag                                                       15

<210> SEQ ID NO 15
<211> LENGTH: 15
<212> TYPE: DNA
<213> ORGANISM: Artificial Sequence
<220> FEATURE:
<223> OTHER INFORMATION: Mutant circular oligonucleotide.

<400> SEQUENCE: 15
tcgtcagtta gttag                                                       15

<210> SEQ ID NO 16
<211> LENGTH: 15
<212> TYPE: DNA
<213> ORGANISM: Artificial Sequence
<220> FEATURE:
<223> OTHER INFORMATION: Mutant circular oligonucleotide.

<400> SEQUENCE: 16
```

-continued

```
tcgtcagtga gttag                                                    15

<210> SEQ ID NO 17
<211> LENGTH: 15
<212> TYPE: DNA
<213> ORGANISM: Artificial Sequence
<220> FEATURE:
<223> OTHER INFORMATION: Mutant circular oligonucleotide.

<400> SEQUENCE: 17
tcgtcagtca gttag                                                    15

<210> SEQ ID NO 18
<211> LENGTH: 80
<212> TYPE: DNA
<213> ORGANISM: Artificial Sequence
<220> FEATURE:
<223> OTHER INFORMATION: 5'-Phosphate oligonucleotide.

<400> SEQUENCE: 18
ctcagctgtg taacaacatg aagattgtag gtcagaactc acctgttaga aactgtgaag   60
atcgcttatt atgtcctatc                                               80

<210> SEQ ID NO 19
<211> LENGTH: 80
<212> TYPE: DNA
<213> ORGANISM: Artificial Sequence
<220> FEATURE:
<223> OTHER INFORMATION: 5'-Phosphorothioate oligonucleotide for
      ligation.

<400> SEQUENCE: 19
ctcagctgtg taacaacatg aagattgtag gtcagaactc acctgttaga aactgtgaag   60
atcgcttatt atgtcctatc                                               80

<210> SEQ ID NO 20
<211> LENGTH: 80
<212> TYPE: DNA
<213> ORGANISM: Artificial Sequence
<220> FEATURE:
<223> OTHER INFORMATION: 5'-Phosphate oligonucleotide.

<400> SEQUENCE: 20
tagcacggac atatatgatg gtaccgcagt atgagtatct cctatcacta ctaagtggaa   60
gaaatgtaac tgtttccttc                                               80

<210> SEQ ID NO 21
<211> LENGTH: 80
<212> TYPE: DNA
<213> ORGANISM: Artificial Sequence
<220> FEATURE:
<223> OTHER INFORMATION: 5'-Phosphate oligonucleotide.

<400> SEQUENCE: 21
tagcacggac atatatgatg gtaccgcagt atgagtatct cctatcacta ctaagtggaa   60
gaaatgtaac tgtttccttc                                               80

<210> SEQ ID NO 22
<211> LENGTH: 20
<212> TYPE: DNA
<213> ORGANISM: Artificial Sequence
<220> FEATURE:
<223> OTHER INFORMATION: Oligonucleotide for ligation reaction.
```

<400> SEQUENCE: 22
cacagctgag gataggacat                                              20

<210> SEQ ID NO 23
<211> LENGTH: 28
<212> TYPE: DNA
<213> ORGANISM: Artificial Sequence
<220> FEATURE:
<223> OTHER INFORMATION: Oligonucleotide for ligation reaction.

<400> SEQUENCE: 23
agtccgtgct agaaggaaac aagttaca                                     28

<210> SEQ ID NO 24
<211> LENGTH: 80
<212> TYPE: DNA
<213> ORGANISM: Artificial Sequence
<220> FEATURE:
<223> OTHER INFORMATION: 5'-Phosphate circular oligonucleotide.

<400> SEQUENCE: 24
ctcagctgtg taacaacatg aagattgtag gtcagaactc acctgttaga aactgtgaag    60
atcgcttatt atgtcctatc                                              80

<210> SEQ ID NO 25
<211> LENGTH: 80
<212> TYPE: DNA
<213> ORGANISM: Artificial Sequence
<220> FEATURE:
<223> OTHER INFORMATION: 5'-Phosphorothioate circular oligonucleotide.

<400> SEQUENCE: 25
ctcagctgtg taacaacatg aagattgtag gtcagaactc acctgttaga aactgtgaag    60
atcgcttatt atgtcctatc                                              80

<210> SEQ ID NO 26
<211> LENGTH: 80
<212> TYPE: DNA
<213> ORGANISM: Artificial Sequence
<220> FEATURE:
<223> OTHER INFORMATION: 5'-Phosphate circular oligonucleotide.

<400> SEQUENCE: 26
tagcacggac atatatgatg gtaccgcagt atgagtatct cctatcacta ctaagtggaa    60
gaaatgtaac tgtttccttc                                              80

<210> SEQ ID NO 27
<211> LENGTH: 80
<212> TYPE: DNA
<213> ORGANISM: Artificial Sequence
<220> FEATURE:
<223> OTHER INFORMATION: 5'-Phosphorothioate circular oligonucleotide.

<400> SEQUENCE: 27
tagcacggac atatatgatg gtaccgcagt atgagtatct cctatcacta ctaagtggaa    60
gaaatgtaac tgtttccttc                                              80

<210> SEQ ID NO 28
<211> LENGTH: 20
<212> TYPE: DNA
<213> ORGANISM: Artificial Sequence
<220> FEATURE:

-continued

```
<223> OTHER INFORMATION: Oligonucleotide for ligation reaction.

<400> SEQUENCE: 28
cacagctgag gataggacat                                            20

<210> SEQ ID NO 29
<211> LENGTH: 29
<212> TYPE: DNA
<213> ORGANISM: Artificial Sequence
<220> FEATURE:
<223> OTHER INFORMATION: Oligonucleotide for ligation reaction.

<400> SEQUENCE: 29
acgtcgtccg tgctagaagg aaacacgca                                  29
```